(12) United States Patent
Birkel et al.

(10) Patent No.: US 11,311,749 B2
(45) Date of Patent: *Apr. 26, 2022

(54) AEROSOL HAIRSPRAY FOR STYLING AND/OR SHAPING HAIR

(71) Applicant: The Procter and Gamble Company, Cincinnati, OH (US)

(72) Inventors: Susanne Birkel, Darmstadt (DE); Wassiliki Christopoulou, Griesheim (DE); Paolo Dal Bò, Frankfurt am Main (DE); Klaus Gänger, Pfungstadt (DE); Bettina Giesen, Bischofsheim (DE)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,993

(22) Filed: Aug. 16, 2019

(65) Prior Publication Data

US 2019/0384880 A1    Dec. 19, 2019

Related U.S. Application Data

(63) Continuation of application No. 13/614,295, filed on Sep. 13, 2012, now Pat. No. 10,426,979.

(30) Foreign Application Priority Data

| Sep. 15, 2011 | (EP) | ..................................... 11007522 |
| Dec. 6, 2011 | (EP) | ..................................... 11192063 |
| Sep. 13, 2012 | (EP) | ..................................... 12184233 |

(51) Int. Cl.
| *A61Q 5/06* | (2006.01) |
| *A61K 8/04* | (2006.01) |
| *A61K 8/19* | (2006.01) |
| *A61K 8/33* | (2006.01) |
| *A61K 8/81* | (2006.01) |
| *A61K 8/87* | (2006.01) |
| *B05B 1/34* | (2006.01) |
| *B65D 83/14* | (2006.01) |
| *G06F 30/23* | (2020.01) |

(52) U.S. Cl.
CPC ............... *A61Q 5/06* (2013.01); *A61K 8/046* (2013.01); *A61K 8/19* (2013.01); *A61K 8/33* (2013.01); *A61K 8/8152* (2013.01); *A61K 8/8158* (2013.01); *A61K 8/87* (2013.01); *B05B 1/3415* (2013.01); *B05B 1/3431* (2013.01); *B65D 83/753* (2013.01); *G06F 30/23* (2020.01); *A61K 2800/30* (2013.01); *A61K 2800/87* (2013.01)

(58) Field of Classification Search
None
See application file for complete search history.

(56) References Cited

U.S. PATENT DOCUMENTS

| 3,120,348 A | 2/1964 | O'Donnell |
| 3,137,416 A | 6/1964 | Shepherd et al. |
| 3,146,922 A | 9/1964 | Tuttle, Jr. |
| 3,472,243 A | 10/1969 | Wall et al. |
| 3,472,604 A | 10/1969 | Dasher et al. |
| 3,475,114 A | 10/1969 | Bolinger et al. |
| 3,537,809 A | 11/1970 | Cednas et al. |
| 3,583,408 A | 6/1971 | Wall |
| 3,587,942 A | 6/1971 | Gailitis |
| 3,619,114 A | 11/1971 | Anzuino et al. |
| 3,619,117 A | 11/1971 | Anzuino et al. |
| 3,619,118 A | 11/1971 | Anzuino et al. |
| 3,633,591 A | 1/1972 | Anzuino et al. |
| 3,634,022 A | 1/1972 | Robbins et al. |
| 3,661,161 A | 5/1972 | Kalopissis et al. |
| 3,676,550 A | 7/1972 | Anzuino |
| 3,678,157 A | 7/1972 | Kalopissis et al. |
| 3,680,738 A | 8/1972 | Vos et al. |
| 3,819,090 A | 6/1974 | Birrell |
| 3,820,550 A | 6/1974 | Kinney et al. |
| 3,876,168 A | 4/1975 | Powers, Jr. |

(Continued)

FOREIGN PATENT DOCUMENTS

| DE | 3048011 A | 7/1982 |
| DE | 4121834 A1 | 1/1993 |

(Continued)

OTHER PUBLICATIONS

"Canadian Application Serial No. 2,848,870, Office Action dated Feb. 8, 2016", 5 pgs.
"Canadian Application Serial No. 2,848,870, Office Action dated Apr. 22, 2015", 5 pgs.
"Canadian Application Serial No. 2,848,870, Office Action dated Aug. 30, 2016", 5 pgs.
"Canadian Application Serial No. 2,848,870, Response filed Aug. 8, 2016 to Office Action dated Feb. 8, 2016", 11 pgs.
"Canadian Application Serial No. 2,848,870, Response flied Oct. 22, 2015 to Office Action dated Apr. 22, 2015", 14 pgs.

(Continued)

*Primary Examiner* — Jyothsna A Venkat
(74) *Attorney, Agent, or Firm* — John G. Powell

(57) ABSTRACT

An aerosol hairspray product for styling and/or shaping hair wherein the product comprises: a container; a spraying device; a propellant; a hairstyling formulation comprising: (a) at least about 50% water; and (b) from about 0.01% to about 20% of a hairstyling polymer, wherein the hairstyling polymer is selected from the group consisting of: acrylates copolymers of two or more monomers of (meth)acrylic acid or one of their simple esters; acrylates/hydroxyesters acrylates copolymers of butyl acrylate, methyl methacrylate, methacrylic acid, ethyl acrylate and hydroxyethyl methacrylate; polyurethane-14/AMP-acrylates polymer blend; and mixtures thereof. The product comprises about 2% or less alcohol, or is substantially free of alcohol, and the product comprises 54% or less VOC.

8 Claims, 7 Drawing Sheets

(56) References Cited

U.S. PATENT DOCUMENTS

| | | |
|---|---|---|
| 3,882,114 A | 5/1975 | Kalopissis et al. |
| 3,909,195 A | 9/1975 | Machell et al. |
| 4,152,416 A | 5/1979 | Marra et al. |
| 4,167,692 A | 9/1979 | Sekiya et al. |
| 4,257,560 A | 3/1981 | Diamond |
| 4,260,110 A | 4/1981 | Werding |
| 4,278,659 A | 7/1981 | Breuer |
| 4,338,295 A | 7/1982 | Highley et al. |
| 4,393,984 A | 7/1983 | Debard |
| 4,417,674 A | 11/1983 | Giuffredi |
| 4,588,760 A | 5/1986 | Jachowicz et al. |
| 4,699,936 A | 10/1987 | Vasta |
| 4,719,104 A | 1/1988 | Patel |
| 4,726,945 A | 2/1988 | Patel et al. |
| 4,801,853 A | 1/1989 | Lewis et al. |
| 4,890,049 A | 12/1989 | Auinger |
| 5,002,761 A | 3/1991 | Mueller et al. |
| 5,068,099 A | 11/1991 | Sramek |
| 5,068,587 A | 11/1991 | Nakamura et al. |
| 5,094,364 A | 3/1992 | Knickerbocker |
| 5,105,988 A | 4/1992 | Knickerbocker |
| 5,126,124 A | 6/1992 | Tazi et al. |
| 5,182,098 A | 1/1993 | Kopolow et al. |
| 5,199,615 A | 4/1993 | Downing |
| 5,207,785 A | 5/1993 | Knickerbocker |
| 5,223,247 A | 6/1993 | Kopolow et al. |
| 5,304,368 A | 4/1994 | Shernov et al. |
| 5,306,972 A | 4/1994 | Hokanson et al. |
| 5,335,858 A | 8/1994 | Dunning et al. |
| 5,348,731 A | 9/1994 | Patti et al. |
| 5,362,486 A | 11/1994 | Nandagiri et al. |
| 5,385,303 A | 1/1995 | Gosselin et al. |
| 5,411,185 A | 5/1995 | Drobish |
| 5,413,775 A | 5/1995 | Hatfield et al. |
| 5,441,728 A | 8/1995 | Tsaur et al. |
| 5,458,871 A | 10/1995 | Malawer et al. |
| 5,462,727 A | 10/1995 | Engler |
| 5,468,791 A | 11/1995 | Yuan |
| 5,525,657 A | 6/1996 | Anchor et al. |
| 5,526,985 A | 6/1996 | Martin |
| 5,560,544 A | 10/1996 | Merritt et al. |
| 5,614,799 A | 3/1997 | Anderson et al. |
| 5,637,296 A | 6/1997 | Rocafort |
| 5,665,804 A | 9/1997 | Hill et al. |
| 5,676,311 A | 10/1997 | Hartman |
| 5,735,465 A | 4/1998 | Laforcade |
| 5,752,396 A | 5/1998 | Schmid et al. |
| 5,901,907 A | 5/1999 | Hildebrandt |
| 5,912,522 A | 6/1999 | Rivera |
| 5,918,774 A | 7/1999 | Lund et al. |
| 5,927,604 A | 7/1999 | Laidler |
| 5,939,058 A | 8/1999 | Schwartz |
| 6,000,633 A | 12/1999 | Lund et al. |
| 6,106,577 A | 8/2000 | Audousset et al. |
| 6,126,921 A | 10/2000 | Emmerling et al. |
| 6,136,884 A | 10/2000 | Chen et al. |
| 6,158,625 A | 12/2000 | Siegel et al. |
| 6,165,446 A | 12/2000 | Samain et al. |
| 6,199,766 B1 | 3/2001 | Fox |
| 6,215,261 B1 | 4/2001 | Becerra |
| 6,223,951 B1 | 5/2001 | Siegel et al. |
| 6,264,067 B1 | 7/2001 | Lasserre |
| 6,346,234 B1 | 2/2002 | Rollat et al. |
| 6,350,439 B1 | 2/2002 | Dupuis |
| 6,440,404 B1 | 8/2002 | Dupuis |
| 6,482,808 B1 | 11/2002 | Springob et al. |
| 6,495,119 B1 | 12/2002 | Sturla et al. |
| 6,503,479 B1 | 1/2003 | Lesaulnier et al. |
| 6,509,012 B1 | 1/2003 | Hoessel et al. |
| 6,512,034 B1 | 1/2003 | Hamada et al. |
| 6,543,703 B2 | 4/2003 | Blake |
| 6,558,697 B2 | 5/2003 | Cannell et al. |
| 6,653,353 B2 | 11/2003 | Adams et al. |
| 6,655,552 B2 | 12/2003 | Aiken et al. |
| 6,727,668 B1 | 4/2004 | Maslov et al. |
| 6,740,317 B1 | 5/2004 | Cho et al. |
| 6,852,815 B1 | 2/2005 | Chuang et al. |
| 6,913,711 B2 | 7/2005 | Mckie et al. |
| 6,966,465 B2 | 11/2005 | Kang, III |
| 7,014,127 B2 | 3/2006 | Valpey, III et al. |
| 7,028,866 B2 | 4/2006 | Kunesh et al. |
| 7,102,307 B2 | 9/2006 | Shao |
| 7,169,380 B2 | 1/2007 | Rollat et al. |
| 7,205,271 B2 | 4/2007 | Drzewinski et al. |
| 7,255,869 B2 | 8/2007 | Uchida et al. |
| 7,303,087 B2 | 12/2007 | Flashinski et al. |
| 7,364,055 B2 | 4/2008 | Yquel et al. |
| 7,423,082 B2 | 9/2008 | Lai |
| 7,448,517 B2 | 11/2008 | Shieh et al. |
| 7,452,525 B1 | 11/2008 | Berezkin et al. |
| 7,487,891 B2 | 2/2009 | Yerby et al. |
| 7,621,468 B2 | 11/2009 | Smith et al. |
| 7,888,904 B2 | 2/2011 | Mularcik |
| 7,926,741 B2 | 4/2011 | Laidler |
| 7,972,589 B2 | 7/2011 | Leighton et al. |
| 7,981,167 B2 | 7/2011 | Carballada et al. |
| 8,048,846 B2 | 11/2011 | Chahal et al. |
| 8,114,938 B2 | 2/2012 | Berezkin et al. |
| D658,009 S | 4/2012 | Davis et al. |
| 8,173,583 B2 | 5/2012 | Garcia et al. |
| 8,241,613 B2 | 8/2012 | Candau et al. |
| 8,318,879 B2 | 11/2012 | Hashemzadeh |
| 8,328,120 B2 | 12/2012 | Vanblaere et al. |
| D681,344 S | 5/2013 | Davis et al. |
| 8,440,211 B2 | 5/2013 | Auguste |
| 8,981,696 B2 | 3/2015 | Bates et al. |
| 9,259,481 B2 | 2/2016 | Shin et al. |
| 9,694,087 B2 | 7/2017 | Shin et al. |
| 9,986,809 B2 | 6/2018 | Brown |
| 10,131,488 B2 | 11/2018 | Brown |
| 10,426,979 B2 * | 10/2019 | Birkel .................... A61K 8/046 |
| 2002/0028187 A1 | 3/2002 | Nekludoff et al. |
| 2002/0085988 A1 | 7/2002 | Nambu |
| 2002/0125462 A1 | 9/2002 | McKie et al. |
| 2002/0150542 A1 | 10/2002 | Steinmetz et al. |
| 2002/0176834 A1 | 11/2002 | Adams et al. |
| 2003/0082223 A1 | 5/2003 | Healy et al. |
| 2003/0103930 A1 | 6/2003 | Uchida et al. |
| 2003/0106901 A1 | 6/2003 | Meshberg |
| 2003/0175229 A1 | 9/2003 | Giroud |
| 2003/0215399 A1 | 11/2003 | Smith et al. |
| 2003/0215400 A1 | 11/2003 | Schroeder et al. |
| 2004/0013615 A1 | 1/2004 | Dubief et al. |
| 2004/0016062 A1 | 1/2004 | Plos |
| 2004/0042974 A1 | 3/2004 | Dupuis |
| 2004/0115151 A1 | 6/2004 | Giroud |
| 2004/0136921 A1 | 7/2004 | Schulz et al. |
| 2004/0144863 A1 | 7/2004 | Kendrick et al. |
| 2004/0166071 A1 | 8/2004 | Pfaffernoschke et al. |
| 2004/0245294 A1 | 12/2004 | Mineau et al. |
| 2004/0261198 A1 | 12/2004 | Kainz et al. |
| 2005/0023368 A1 | 2/2005 | Valpey, III et al. |
| 2005/0052080 A1 | 3/2005 | Maslov et al. |
| 2005/0063916 A1 | 3/2005 | Ishii |
| 2005/0137198 A1 | 6/2005 | Nelson |
| 2005/0255067 A1 | 11/2005 | Leighton |
| 2006/0060554 A1 | 3/2006 | Garman |
| 2006/0076171 A1 | 4/2006 | Donnelly et al. |
| 2006/0105003 A9 | 5/2006 | Rollat-Corvol et al. |
| 2007/0018017 A1 | 1/2007 | Tilton et al. |
| 2007/0066506 A1 | 3/2007 | Behler et al. |
| 2007/0241132 A1 | 10/2007 | Smith |
| 2007/0245538 A1 | 10/2007 | Salameh |
| 2007/0267447 A1 | 11/2007 | Kennedy |
| 2007/0275020 A1 | 11/2007 | Lendlein et al. |
| 2007/0277332 A1 | 12/2007 | Bimczok et al. |
| 2007/0286833 A1 | 12/2007 | Keller et al. |
| 2007/0292641 A1 | 12/2007 | Altonen et al. |
| 2008/0003387 A1 | 1/2008 | Altonen et al. |
| 2008/0008781 A1 | 1/2008 | Sweeney |
| 2008/0017666 A1 | 1/2008 | Vanblaere et al. |
| 2008/0020004 A1 | 1/2008 | Birkel et al. |
| 2008/0035638 A1 | 2/2008 | Burghaus et al. |
| 2008/0041884 A1 | 2/2008 | Chevalier |

(56) References Cited

U.S. PATENT DOCUMENTS

| | | |
|---|---|---|
| 2008/0102051 A1 | 5/2008 | Huynh et al. |
| 2008/0112898 A1 | 5/2008 | Schiemann |
| 2008/0116759 A1 | 5/2008 | Lin |
| 2008/0152610 A1 | 6/2008 | Cajan et al. |
| 2008/0166305 A1 | 7/2008 | Singh et al. |
| 2008/0187505 A1 | 8/2008 | Speckbacher et al. |
| 2008/0187506 A1 | 8/2008 | Carballada et al. |
| 2008/0197152 A1 | 8/2008 | Neuhaus et al. |
| 2008/0210253 A1 | 9/2008 | Carballada et al. |
| 2008/0219934 A1 | 9/2008 | Kim et al. |
| 2008/0279804 A1 | 11/2008 | Parker et al. |
| 2008/0311050 A1 | 12/2008 | Lendlein et al. |
| 2009/0010865 A1 | 1/2009 | Kim et al. |
| 2009/0022681 A1 | 1/2009 | Carballada et al. |
| 2009/0041689 A1 | 2/2009 | Berezkin et al. |
| 2009/0050599 A1 | 2/2009 | Martin et al. |
| 2009/0050634 A1 | 2/2009 | Girardot et al. |
| 2009/0050638 A1 | 2/2009 | Smith et al. |
| 2009/0060858 A1 | 3/2009 | Schwarzwaelder et al. |
| 2009/0060859 A1 | 3/2009 | Garcia et al. |
| 2009/0074697 A1 | 3/2009 | Huynh |
| 2009/0084870 A1 | 4/2009 | Smith et al. |
| 2009/0084872 A1 | 4/2009 | Vanblaere et al. |
| 2009/0104138 A1 | 4/2009 | Shimatani et al. |
| 2009/0118044 A1 | 5/2009 | Kuo et al. |
| 2009/0124961 A1 | 5/2009 | Harman |
| 2009/0144961 A1 | 6/2009 | Pinard et al. |
| 2009/0160392 A1 | 6/2009 | Mularcik |
| 2009/0295315 A1 | 12/2009 | Tarnow et al. |
| 2009/0297467 A1 | 12/2009 | Laurent et al. |
| 2010/0028286 A1 | 2/2010 | Carballada et al. |
| 2010/0048988 A1 | 2/2010 | Pastorelli |
| 2010/0052584 A1 | 3/2010 | Bates et al. |
| 2010/0116909 A1 | 5/2010 | Abduljalil |
| 2010/0123426 A1 | 5/2010 | Nashiki et al. |
| 2010/0135472 A1 | 6/2010 | Winter et al. |
| 2010/0189664 A1 | 7/2010 | Castro et al. |
| 2010/0219211 A1 | 9/2010 | Smith |
| 2011/0027211 A1 | 2/2011 | Viala et al. |
| 2011/0064684 A1 | 3/2011 | Krause et al. |
| 2011/0114759 A1 | 5/2011 | Schmitz |
| 2011/0158928 A1 | 6/2011 | Mueller et al. |
| 2011/0192415 A1 | 8/2011 | Verboom |
| 2011/0205662 A1 | 8/2011 | Bates et al. |
| 2011/0241592 A1 | 10/2011 | Lin |
| 2011/0248099 A1 | 10/2011 | Ghavami-nasr |
| 2011/0303148 A1 | 12/2011 | Xie |
| 2011/0303766 A1 | 12/2011 | Smith |
| 2011/0303767 A1 | 12/2011 | Smith |
| 2012/0031419 A1* | 2/2012 | Batt .................. A61K 8/8182 132/203 |
| 2012/0034173 A1* | 2/2012 | Batt .................. A61Q 5/06 424/47 |
| 2012/0111898 A1 | 5/2012 | Neuhaus |
| 2012/0180807 A1 | 7/2012 | Flohr |
| 2012/0183486 A1 | 7/2012 | Flohr et al. |
| 2012/0263669 A1 | 10/2012 | Mueller |
| 2013/0058882 A1 | 3/2013 | Flohr et al. |
| 2013/0068243 A1 | 3/2013 | Birkel |
| 2013/0068849 A1 | 3/2013 | Birkel et al. |
| 2013/0340785 A1 | 12/2013 | Baum |
| 2014/0070025 A1 | 3/2014 | Dalbo |
| 2014/0199251 A1 | 7/2014 | Ashida |
| 2015/0000687 A1 | 1/2015 | Brown et al. |
| 2015/0004200 A1 | 1/2015 | Brown et al. |
| 2015/0232260 A1 | 8/2015 | Dann et al. |
| 2016/0175238 A1 | 6/2016 | Shin et al. |
| 2016/0250120 A1 | 9/2016 | Knappe et al. |
| 2016/0263009 A1 | 9/2016 | Saito et al. |
| 2016/0303023 A1 | 10/2016 | Bevinakatti |
| 2016/0346175 A1 | 12/2016 | Sasik et al. |
| 2016/0347536 A1 | 12/2016 | Brown et al. |
| 2018/0263355 A1 | 9/2018 | Brown |
| 2019/0384880 A1 | 12/2019 | Birkel |

FOREIGN PATENT DOCUMENTS

| | | |
|---|---|---|
| DE | 4431577 A1 | 3/1996 |
| DE | 29615896 U1 | 1/1998 |
| DE | 29707765 U1 | 9/1998 |
| DE | 10259199 A1 | 6/2004 |
| DE | 102004036004 A1 | 2/2006 |
| DE | 102005018205 A1 | 10/2006 |
| DE | 102008024650 A1 | 4/2010 |
| EP | 0379627 A1 | 8/1990 |
| EP | 0574607 A1 | 12/1993 |
| EP | 0688577 A1 | 12/1995 |
| EP | 1026220 A1 | 8/2000 |
| EP | 0873946 B1 | 7/2001 |
| EP | 1220956 B1 | 7/2003 |
| EP | 0832639 B1 | 1/2004 |
| EP | 1161934 B1 | 4/2004 |
| EP | 1092650 B1 | 12/2005 |
| EP | 1160178 B1 | 7/2006 |
| EP | 1681078 B1 | 12/2008 |
| EP | 1719500 B1 | 6/2010 |
| EP | 2228319 B1 | 5/2013 |
| FR | 2784081 B1 | 4/2000 |
| JP | H02262003 A | 10/1990 |
| JP | H0454116 A | 2/1992 |
| JP | H04208214 A | 7/1992 |
| JP | H076881 A | 1/1995 |
| JP | H10279436 A | 10/1998 |
| JP | H10337509 A | 12/1998 |
| JP | H11228398 A | 8/1999 |
| JP | 2000343007 A | 12/2000 |
| JP | 2001227475 A | 8/2001 |
| JP | 2001302458 A | 10/2001 |
| JP | 2002347866 A | 12/2002 |
| JP | 2003054668 A | 2/2003 |
| JP | 2004195287 A | 7/2004 |
| JP | 3727112 B2 | 10/2005 |
| JP | 3828257 B2 | 7/2006 |
| JP | 2007117940 A | 5/2007 |
| JP | 3969517 B2 | 6/2007 |
| JP | 2007296428 A | 11/2007 |
| JP | 4278878 B2 | 3/2009 |
| JP | 2011190195 A | 9/2011 |
| JP | 5321122 | 10/2013 |
| JP | 5883234 B2 | 3/2016 |
| WO | 8905195 A1 | 6/1989 |
| WO | 9725259 A1 | 7/1997 |
| WO | 9729029 A1 | 8/1997 |
| WO | 9800354 A1 | 1/1998 |
| WO | WO9967216 A1 | 12/1999 |
| WO | 200045777 A1 | 8/2000 |
| WO | 200153157 A2 | 7/2001 |
| WO | WO0170179 A1 | 9/2001 |
| WO | 200213773 A2 | 2/2002 |
| WO | 200245665 A1 | 6/2002 |
| WO | 03015929 A1 | 2/2003 |
| WO | 03061839 A1 | 7/2003 |
| WO | 2004043330 A2 | 5/2004 |
| WO | 2004062633 A1 | 7/2004 |
| WO | 2006073174 A1 | 7/2006 |
| WO | 2007062731 A1 | 6/2007 |
| WO | 2007099268 A2 | 9/2007 |
| WO | 2007099269 A2 | 9/2007 |
| WO | 2007099271 A2 | 9/2007 |
| WO | 2011056625 A1 | 5/2011 |
| WO | 2012009302 A1 | 1/2012 |
| WO | 2014210309 A2 | 12/2014 |

OTHER PUBLICATIONS

"Canadian Application Serial No. 2,848,870, Voluntary Amendment filed Jun. 24, 2014", 7 pgs.

"Chinese Application Serial No. 201280044125.3, Argument and Amendment filed Mar. 22, 2016 in response to Office Action dated Jan. 20, 2016", (w/ English Translation of Amended Claims), 11 pgs.

(56) References Cited

OTHER PUBLICATIONS

"Chinese Application Serial No. 201280044125.3, Argument and Amendment filed Jun. 16, 2015 in response to Office Action dated Dec. 25, 2014", (w/ English Translation of Argument), 12 pgs.
"Chinese Application Serial No. 201280044125.3, Argument filed Oct. 20, 2015—in response to Office Action dated Aug. 21, 2015", (wi English Translation), 9 pgs.
"Chinese Application Serial No. 201280044125.3, Office Action dated Jan. 20, 2016", (w/ English Translation), 18 pgs.
"Chinese Application Serial No. 201280044125.3, Office Action dated Aug. 21, 2015", (w/ English Translation), 19 pgs.
"Chinese Application Serial No. 201280044125.3, Office Action dated Dec. 25, 2014", (w/ Englist1 Translation), 20 pgs.
"European Application Serial No. 11192063.3, Communication Pursuant to Article 94(3) EPC dated Jun. 11, 2015", 6 pgs.
"European Application Serial No. 11192063.3, Communication Pursuant to Article 94(3) EPC dated Sep. 9, 2014", 4 pgs.
"European Application Serial No. 11192063.3, Response filed Mar. 19, 2015 to Communication Pursuant to Article 94(3) EPC dated Sep. 9, 2014", 3 pgs.
"European Application Serial No. 11192063.3, Response filed Sep. 16, 2016 to Summons to Attend Oral Proceedings mailed Apr. 1, 2016", 21 pgs.
"European Application Serial No. 11192063.3, Response filed Dec. 15, 2015 to Communication Pursuant to Article 94(3) EPC dated Jun. 11, 2015", 9 pgs.
"European Application Serial No. 11192063.3, Summons to Attend Oral Proceedings mailed Apr. 1, 2016", 8 pgs.
"European Application Serial No. 11192065.8, Examination Notification Art. 94(3) mailed Oct. 31, 2013", 5 pgs.
"European Application Serial No. 11192065.8, Intention to Grant dated Dec. 23, 2014", 65 pgs.
"European Application Serial No. 11192065.8, Office Action dated Nov. 7, 2014", 2 pgs.
"European Application Serial No. 11192065.8, Response filed May 12, 2014 to Examination Notification Art. 94(3) mailed Oct. 31, 2013", 3 pgs.
"European Application Serial No. 11192065.8, Response filed Sep. 19, 2013 to Extended European Search Report dated Dec. 6, 2012", 11 pgs.
"European Application Serial No. 11192065.8, Response filed Oct. 17, 2014 to Summons toAttend Oral Proceedings mailed Jun. 18, 2014", 28 pgs.
"European Application Serial No. 11192065.8, Summons to Attend Oral Proceedings mailed Jun. 18, 2014", 4 pgs.
"European Application Serial No. 11192065.8, Written Submission filed Nov. 13, 2014", 96 pgs.
"European Application Serial No. 12184231.4, Amendments filed Nov. 12, 2014", 15 pgs.
"European Application Serial No. 12184231.4, Communication Pursuant to Article 94(3) EPC dated Oct. 31, 2013", 5 pgs.
"European Application Serial No. 12184231.4, Intention to grant dated Jan. 5, 2015", 50 pgs.
"European Application Serial No. 12184233.0, Further Result of Consultation mailed Oct. 12, 2016", 3 pgs.
"European Application Serial No. 12184233.0, Result of Consultation mailed Oct. 17, 2016", 3 pgs.
"European Application Serial No. 121842330, Summons to Attend Oral Proceedings mailed Apr. 14, 2016", 8 pgs.
"Japanese Application Serial No. 2014-530001, Office Action dated Jun. 23, 2015", w English Translation, 11 pgs.
"Japanese Application Serial No. 2014-530001, Office Action dated Dec. 2, 2014", 10 pgs.
"Japanese Application Serial No. 2014-530001, Response filed Jan. 23, 2015 to Office Action dated Dec. 2, 2014", 12 pgs.
"Japanese Application Serial No. 2014-530001, Response filed Jul. 22, 2015 to Office Action dated Jun. 23, 2015", 7 pgs.
"Japanese Application Serial No. 2014-530003, Office Action dated Apr. 7, 2015", (wi English Translation), 11 pgs.
"Japanese Application Serial No. 2014-530003, Written Argument and Amendment filed Jun. 15, 2015 to Office Action dated Apr. 7, 2015", (wi Englisth Translation of Argument), 26 egs.
"Mexican Application Serial No. MX/a/2014/003230, Office Action dated Dec. 7, 2016",(English Translation), 1 pg.
"Mexican Application Serial No. MX/a/2014/003230, Response filed Mar. 3, 2017 to Office Action dated Dec. 7, 2016", (w/ English Translation of Amended Claims), 13 pgs.
All final and non-final office actions for U.S. Appl. No. 13/180,931.
All final and non-final office actions for U.S. Appl. No. 13/181,058.
All final and non-final office actions for U.S. Appl. No. 13/614,249.
All final and non-final office actions for U.S. Appl. No. 13/614,925.
All final and non-final office actions for U.S. Appl. No. 14/315,950.
All final and non-final office actions for U.S. Appl. No. 15/170,031.
International Preliminary Report on Patentability for PCT/US2012/055075 dated Mar. 27, 2014.
PCT International Search Report and Written Opinion for PCT/US2012/055075 dated Dec. 6, 2012.
Troy, Remington: The Science and Practice of Pharmacy Baltimore: Lipponcott Williams & Wilkins, 2006, p. 1009 (Year: 2006).
Chadwick. Spray Technology & Marketing Dec. 2004, p. 1-3 (year 2004).
Rance. Journal of the Society of Cosmetic Chemists, vol. 23, No. 4, 197-208 (year: 1972).
"Personal Care Polymers", Product Catalog, National Starch & Chemical, 2000, 16 pages.
All Office Actions, U.S. Appl. No. 14/315,917.
All Office Actions, U.S. Appl. No. 15/967,671.
Andrea Keenan; Hair Styling Formulations Containing Acudyne 180 Hair Fixative Polymer and Aculyn Rheology Modifiers; RD478088; Feb. 10, 2004, 6 pages.
CAS Registry entry for 1,2-difluoroethane, American Chemical Society, 2014, 6 pages.
CAS Registry entry for dimethyl ether, American Chemical Society, 2014, 6 pages.
EP Search Report for EP12184233.0 dated Nov. 29, 2013, 6 pages.
PCT Search Report for PCT/US2012/055102 dated Nov. 29, 2013, 10 pages.
Cook Philip M et al: "Low VOC hair-sprays . It depends very much on the choice of polymer", Aerosol Spray Report, Heidelberg, DE, vol. 37, No. 3, Jan. 1, 1998, pp. 20-23.
Miao Wang et al.; Acrylates/Hydroxyesters Acrylates Copolymer in Personal Care Applications: Acudyne DHR Durable Hold Resin; RD478006; Feb. 10, 2004, 16 pages.
Miao Wang; Mousse Formulations Containing Acudyne DHR or Acudyne 180 Hair Fixative Polymer and Aculyn 88 Rheology Modifier; RD510027; Oct. 10, 2006, 5 pages.
Product Introduction: inserts [online], Precision Valve Japan, Ltd., 2006 [Searching date: Jun. 22, 2016], 7 pages.
"The Shellac Story—Shellac Properties", retrieved from the internet: http://www.shellac.in.shellac_properties.html, retrieved on Jul. 11, 2016, 1 page.

\* cited by examiner

AEROSOL HAIRSPRAY FOR STYLING AND/OR SHAPING HAIR

FIELD OF THE INVENTION

An aerosol hairspray product for styling and/or shaping hair.

BACKGROUND OF THE INVENTION

Hairstyling products such as hairsprays are used for achieving different hairstyles and for holding hair strands in place for a period of time. Typically, hairsprays comprise film-forming polymers, which when applied to keratin-containing fibres, such as human hair, form fibre-fibre welds. These welds 'glue' the fibres together and hence impart hold to the hairstyle.

Aerosol hairspray products usually comprise a pressure-resistant container, a nozzle, a propellant, and a hairstyling formulation. A hairspray composition is normally ejected from such products via aerosol-forming nozzle. See, for example, US2009/0104138A1. Commonly used propellants include the volatile organic compounds (VOCs) propane, butane, 1,1-difluoroethane, and dimethylether. However, VOCs are known to react with certain nitrogenic oxides, which in turn may result in the formation of ground-level ozone—a potential source of health problems. Alcohols are also often used in the hairstyling formulation, for example to reduce surface tension. However, a high proportion of alcohol may leave the hair feeling dry and brittle and some alcohols may cause an allergic response in some users. Also, ethanol is flammable and is a VOC.

There is a constant need, therefore, for more environmentally friendly, more sustainable, and affordable hairspray products, in particular for aerosol hairspray products comprising low levels of VOC and alcohol. However, altering one or more features of an aerosol hairspray product can be challenging since the interrelationship therebetween affects the product performance. For example, utilising a different propellant may result in an unacceptable droplet size of the ejected composition and consequently unsatisfactory hold. Furthermore, certain hairstyling polymers may be incompatible with hairspray products comprising low levels of VOC and/or alcohol.

When considering the aforementioned needs, therefore, good hairspray performance should be maintained. Performance benefits may include, for example: excellent hold; long-lasting hold; good humidity resistance; shapeable hold; acceptable drying time; excellent soft, natural hair feel; acceptable and/or non-stickiness/tackiness of the hands and hair. Of particular relevance to consumers is natural hair feel and non-tackiness of the hands and hair.

SUMMARY OF THE INVENTION

In a first aspect, the invention relates to an aerosol hairspray product for styling and/or shaping hair wherein the product comprises:
  i. a container comprising a container wall which encloses a reservoir for storing a hairstyling formulation and a propellant;
  ii. the hairstyling formulation comprising:
    (a) at least about 50% water by total weight of the hairstyling formulation and propellant; and
    (b) from about 0.01% to about 20% of a hairstyling polymer by total weight of the hairstyling formulation and propellant, wherein the hairstyling polymer is selected from the group consisting of: acrylates copolymers of two or more monomers of (meth) acrylic acid or one of their simple esters; acrylates/hydroxyesters acrylates copolymers of butyl acrylate, methyl methacrylate, methacrylic acid, ethyl acrylate and hydroxyethyl methacrylate; polyurethane-14/AMP-acrylates polymer blend; and mixtures thereof; and
  iii. a propellant, which is selected from the group consisting of compressed gas propellants, liquefied gas propellants, and mixtures thereof; and
  iv. a spraying device attached to the container for dispensing the hairstyling formulation from the reservoir of the container;

and wherein the product comprises about 2% or less alcohol by total weight of the hairstyling formulation and propellant, or is substantially free of alcohol;
wherein the product comprises 54% or less volatile organic compound by total weight of the hairstyling formulation and propellant.

In a second aspect, the invention relates to a method for styling hair comprising:
  i. applying to hair an ejected composition, wherein the ejected composition is ejected by the hairspray product according to the first aspect;
  ii. drying the ejected composition on the hair.

In a third aspect, the invention relates to the use of the product according to the first aspect for fixing and/or shaping a hairstyle.

BRIEF DESCRIPTION OF THE DRAWINGS

Embodiments of the present invention will now be described, by way of example only, with reference to the drawings in which.

DETAILED DESCRIPTION OF THE INVENTION

Figure 1:
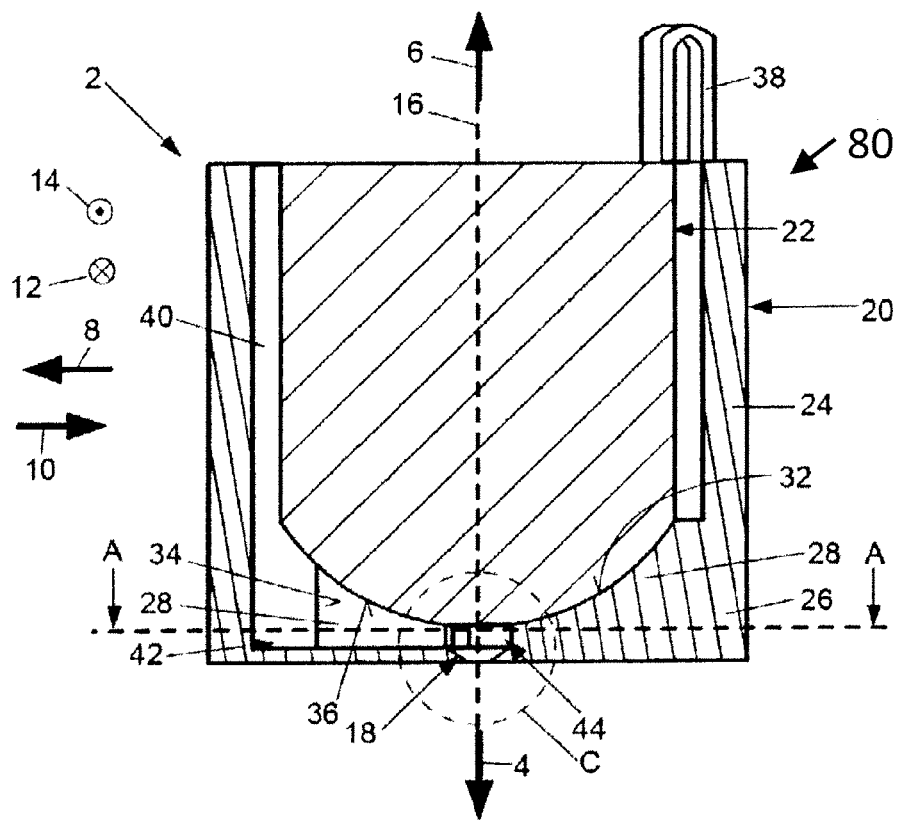
FIG. 1 shows a cross-sectional side-view of an embodiment of a spray nozzle.

All percentages are by weight of the total composition/formulation, unless stated otherwise. All ratios are weight ratios, unless stated otherwise. All ranges are inclusive and combinable. The number of significant digits conveys neither a limitation on the indicated amounts nor on the accuracy of the measurements. The term "molecular weight" or "M. Wt." as used herein refers to the weight average molecular weight unless otherwise stated. "QS" or "QSP" means sufficient quantity for 100%. +/− indicates the standard deviation.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Embodiments and aspects described herein may comprise or be combinable with elements or components of other embodiments and/or aspects despite not being expressly exemplified in combination, unless otherwise stated or an incompatibility is stated.

The term "aerosol" as used herein, means a suspension of fine droplets in a gas. The aerosol hairspray product atomises the hairspray formulation i.e. creates an aerosol. Due to surface tension, droplets are normally substantially spherical. As used herein, the "droplet size" is defined as the median diameter of ejected droplets.

The term "aerosol hairspray product" does not encompass mousse or foam products. The term "mousse" or "foam" as defined herein means a dispersion of gas bubbles in a liquid. Commonly, mousse or foam compositions usually comprise greater than 0.3% surfactant by weight. The surfactant results in the formation of spherical bubbles which form the mousse or foam consistency. However, foams and mousses can also be formed from surfactant-free formulations via other means, for example special actuators, using proteins e.g. egg white protein. Typically, hairstyling products that eject a mousse/foam also comprise from about 6% to about 16% by weight propellant.

The term "aerosol hairspray product" does not encompass gel products or products comprising or ejecting a gel composition. Gels may be dispensed via a pump spray actuator. Hand gel formulations typically have a viscosity of from about 8,000 mPa·s to about 20,000 mPa·s depending on the desired performance. The ejected composition of spray gels typically has a droplet size of at least about 80 micron in diameter.

As used herein, the term "on-hair drying time" means the amount of time it takes for the ejected composition to dry on the hair. The on-hair drying time is measured by spraying a specific pattern on the hair and then timing when the hair ceases to feel tacky and damp in the hand.

As used herein, the term "ejection flow" is defined as the loss in total weight of the aerosol hairspray product after 5 seconds of spraying. This value is normally divided by 5 to give grams per sec. The ejection flow should achieve a balance between excellent hold and sufficiently fast drying time. For example, if too much ejected composition is applied to the hair in a short period, then the on-hair drying time may be unacceptably long.

Herein, "comprising" means that other steps and other ingredients which do not affect the end result can be added. This term encompasses the terms "consisting of" and "consisting essentially of". The compositions, methods, uses, and processes herein can comprise, consist of, and consist essentially of the elements and limitations of the invention described herein, as well as any of the additional or optional ingredients, components, steps, or limitations described herein.

The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The term "hairstyling polymer" as used herein means hair-fixing polymers which form films on a surface. In the context of hair, this surface is the surface of individual hair fibres or a plurality thereof. The polymer causes them to be glued together to build welds, which are cross-links that provide the hold benefit. In concert, these welds form a 'hairnet' to provide hair hold and volume benefits to the user. When the net of welds is effectively formed, the hold and volume benefits can last all day and offer good resistance to environmental humidity.

The hairspray product according to the present invention is suitable for application onto human hair. The term "suitable for application to human hair" as used herein means that the compositions or components thereof so described are suitable for use in contact with human hair and the scalp without undue toxicity, incompatibility, instability, allergic response, and the like.

The term "maximum incremental reactivity" value or "MIR" value as defined herein, means a measure of the increase in ozone formation per unit weight of a hydrocarbon when added to the atmosphere. Hence, MIR measured the ozone forming potential of a compound. A similar measurement to MIR is "photochemical ozone creation potential" or "POCP".

The term "global warming potential" or "GWP" as defined herein is a measure of how much a given mass of a compound is calculated to contribute to global warming compared to that of the same mass of carbon dioxide. The global warming potential of carbon dioxide, therefore, is 1. As used herein, the GWP values are those calculated for a 100 year time horizon, unless otherwise stated.

As used herein, the term "volatile organic compound" or "VOC", as used herein means any organic compound having a initial boiling point less than or equal to 250° C. measured at a standard pressure of 101.3 kPa. In an embodiment, "VOC" means any compound having a vapour pressure of 0.01 kPa or more at 293.15 K (i.e. 20° C.). "Organic" as used herein means any compound containing at least the element carbon and one or more of hydrogen, halogen, oxygen, sulfur, phosphorus, silicon, or nitrogen. Certain volatile compounds of organic chemistry falling within this definition are known to photochemically react with nitrogenic oxides in the presence of sunlight and, in turn, this produces ground-level ozone and photochemical smog. In fact, in the United States, the definition of VOC for US legislative purposes (U.S. EPA 40 CFR 51. 100[s]) defines only those organic compounds without negligible photochemical reactivity. Examples of compounds considered to be VOCs for the purposes of this application include: ethanol, dimethylether, 1,1-difluoroethane, 1,1,1,2-tetrafluoroethane, pentane, n-butane, iso-butane, propane, trans-1,3,3,3-tetrafluoropropene, free formic acid (i.e. not its salt). Certain fragrances and plant extracts are also VOCs.

The term "non-flammable", as used herein in terms of the aerosol hairspray product, means the product contains 1% or less flammable components and the chemical heat of combustion is less than 20 kJ/g and is also considered non-flammable following an ignition distance test and, if necessary, the enclosed space test. If the chemical heat of combustion is less than 20 kJ/g, then the aerosol is classified as flammable if ignition occurs at a distance of 15 cm or more. The ignition distance test for spray aerosols is a standard test wherein the aerosol is sprayed in the direction of an ignition source at intervals of 15 cm to observe if ignition and sustained combustion takes place. Ignition and sustained combustion is defined as when a stable flame is maintained for at least 5 seconds. The ignition source is defined as a gas burner with a blue, non-luminous flame 4-5 cm in height. If no ignition occurs in the ignition distance test, the enclosed space test shall be performed and in this case, the aerosol is classified as flammable if the time equivalent is less than or equal to 300 s/m$^3$ or the deflagration density is less than or equal to 300 g/m$^3$; otherwise the aerosol is classified as non-flammable. The enclosed space ignition test is a standard test wherein the contents of an aerosol dispenser are sprayed into a cylindrical test vessel containing a burning candle. If an observable ignition occurs, the elapsed time and amount discharged is noted. These definitions are that of the UN Manual of Tests and Criteria, Part III, Section 31. The chemical heat of combustion can be determined via the standard method ASTM D 240.

The term "substantially free from", "substantially free of", or grammatical equivalents thereof, as defined herein means less than about 1%, or less than about 0.8%, or less than about 0.5%, or less than about 0.3%, or about 0%.

The inventors have surprisingly overcome the above hindrances and answered the aforementioned needs by carefully selecting the specific combination of mutually compatible features such that the interaction therebetween results in a hairspray with good performance. Firstly, the hairspray formulation pursuant to the present invention is water-based i.e. it is an aqueous system rather than a predominantly alcohol-based system as is conventionally employed. This water-based system provides safety, sustainability, environmental and cost advantages. Secondly, the hairspray product comprises about 2% or less alcohol by total weight of the hairstyling formulation and propellant, or is substantially free of alcohol. This additionally provides highly consumer-relevant benefits since alcohol has the reputation of causing the hair to become brittle and dry, particularly for naturally fine and/or dry hair. Without being bound by theory it is believed that low alcohol concentrations help to reduce drying out effect i.e. reduce a perceived brittle, harsh feel of the hair. Consumers prefer a more natural hair feel and look. The inventors have found that selected hairstyling polymers are particularly suited for use in such hairspray formulation. The inventors have found that hairstyling polymer M. Wt., glass transition temperature, water-compatibility and chemistry are important factors in order to create a low viscosity, fully dissolved, readily sprayable hairstyling formulation that provides an ejected composition that, following normal application onto hair, results in good hairstyle hold, good humidity resistance, no residues or flaking on hair, and yet is easily washed out. The selected hairstyling polymers meet these criteria—in particular, the hairstyling polymers, despite being highly compatible in the water-based hairstyling formulation, also provide humidity resistance in high relative humidity for the hairstyle and yet are easily washed out with normal shampoo. Moreover, the hold offered by the selected hairstyling polymers is good, but without causing a 'helmet head'-type feeling for the consumer. Performance benefits achieved by the hairspray product pursuant to the present invention include excellent hair feel, particularly natural hair feel, and excellent non-stickiness of the hands and hair, good hold and shapeable hold. Furthermore, it has been surprisingly found that the selected polymers can be blended together in order to provide more natural hair feel or greater hairstyle hold. The hairstyling polymers can be blended into specific mixtures, for example 'soft' hairstyling polymers may be blended with 'hard' hairstyling polymers.

A particular benefit of the hairstyling polymers as described herein is the low tackiness on hands and/or hair achieved. Surprisingly the tackiness on hands and/or hair of the present invention is lower than achieved by conventional ethanol-based aerosol hairsprays. This is surprising because the hold provided by the present invention is comparable to conventional aerosol hairsprays.

Each of the features of the aerosol hairspray product, as well as other relevant components, are described in detail hereinafter.

According to the first aspect, the present invention relates to an aerosol hairspray product, wherein the product comprises less than 54% VOC by total weight of the hairstyling formulation and propellant. In an embodiment, the aerosol hairspray product has a maximum incremental reactivity (MIR) value of less than 1, or less than 0.8, or less than 0.7, or less than 0.4. The MIR value of an aerosol hairspray product can be calculated by multiplying the fraction by weight of each component of the hairspray product by its MIR value. MIR values of common components of hairspray products include: 2-aminomethyl propanol: about 15.08; water: 0.00; acetone: 0.43; ethanol: 1.69; isopropanol: 0.71. More MIR values are listed below. For example, a product comprising 0.2% of 2-aminomethyl propanol and no other components with an MIR value above zero, would have an MIR value of 0.03. In an embodiment, the hairstyling formulation and propellant have a heat of combustion of from about 5 kJ/kg to about 20 kJ/kg and/or the product is non-flammable.

The surface tension and viscosity of the hairstyling formulation can be important because following spraying, the ejected composition forms droplets, which land on the hair. The ejected composition should then spread out along each individual hair fibre in order to form a thin layer of coating on the hair, which dries quickly and also forms welds with other similarly coated hair fibres. In an embodiment, the surface tension, measured according to standard test ISO 304 at 20° C., of the hairstyling formulation is from about 20 mN/m to about 50 mN/m, or from about 20 mN/m to about 40 mN/m, or from about 28 mN/m to about 40 mN/m, or from about 30 mN/m to about 40 mN/m. ISO 304 is a standard test method for measuring surface tension of pure liquids or solutions.

In an embodiment, the kinematic viscosity, measured according to standard test DIN EN ISO 3104, of the hairstyling formulation is from about 1 mm$^2$/s to about 25 mm$^2$/s, or from about 1 mm$^2$/s to about 15 mm$^2$/s, or from about 2 mm$^2$/s to about 10 mm$^2$/s, or from about 1 mm$^2$/s to about 4 mm$^2$/s, or from about 1.2 mm$^2$/s to about 3 mm$^2$/s. DIN EN ISO 3104 is a standard test method for measuring kinematic viscosity of liquids. The kinematic viscosity can be important because when the hairstyling formulation is too viscous then the hairstyling formulation is too thick and cannot be sprayed and/or is clogging—inhomogeneous ejected formulation results e.g. irregular spray beam, "spitting" rather than spraying, and/or ejection of lumps. This can be especially important when a compressed gas propellant is utilised because the propellant is in gaseous form and hence cannot function as a co-solvent.

The median droplet size of the ejected composition is from about 10 micron to about 80 micron, or from about 15 micron to about 60 micron, or from about 15 micron to about 50 micron, or from about 20 micron to about 35 micron. Droplets smaller than about 10 micron are not suitable for the present invention due to safety concerns—the droplets may enter the lungs and cause health problems. Droplets larger than about 100 micron are too large and consequently unsuitable. In an embodiment, the droplet size is not greater than 80 micron. Hairspray products which are pump sprays normally have a droplet size which is too large and are hence unsuitable. The aerosol hairspray product is not a pump spray.

Droplet size is measured using a technique based on laser diffraction. Scattered light is focused by a focusing lens in a Fourier arrangement and picked up by the detector array. The angle at which a particle/droplet diffracts light is inversely proportional to its size. The detector array is made up of over 30 individual detectors, each of which collects the light scattered by a particular range of angles. The scattering pattern from the spray is captured, which is what is measured. Measuring the angle of diffraction determines the size of the particle/droplet. A Malvern Spraytec EPCS 4.0 is used with a 450 mm lens type, serial number 237. Software: RT Sizer 5.0. Test duration: 4000 ms. Data acquisition rate: 200 Hz. Minimum droplet size able to be measured: 0.8 micron. Maximum droplet size able to be measured: 300 micron. Distance between nozzle and laser beam: 140 mm.

The ejection flow of the hairspray product is from about 0.10 g/sec to about 0.40 g/sec, or from about 0.20 g/sec to about 0.35 g/sec, or from about 0.20 g/sec to about 0.30 g/sec, or from about 0.20 g/sec to about 0.25 g/sec. If the ejection flow is greater than about 0.45 g/sec, then the on-hair drying time will be too long for consumer satisfaction. Ejection flow can typically be adjusted by altering the pressure inside the container (increased pressure correlates with faster ejection flow) and/or the diameter opening in the spraying device and/or orifices in the actuator (lower diameter correlates with slower ejection flow).

The on-hair drying time of the ejected composition may be from about 0.5 min to about 7 min, or from about 1 min to about 5 min, or from about 1 min to about 2 min.

The hairstyling formulation comprises from about 0.01% to about 20%, or from about 1% to about 16%, or from about 2% to about 12%, or from about 3% to about 8%, or from about 4% to about 7% of a hairstyling polymer, by total weight of the hairstyling formulation and propellant.

The hairstyling polymer is selected from the group consisting of: acrylates copolymers of two or more monomers of (meth)acrylic acid or one of their simple esters; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof. Balance® CR from Akzo Nobel is an acrylates copolymer of two or more monomers of (meth)acrylic acid or one of their simple esters. In an embodiment, polyurethane-14/AMP-acrylates copolymer blend is blend of an acrylates copolymer and a polyurethane polymer. Acudyne™ 1000 is an acrylates/hydroxyesters acrylates copolymer of butyl acrylate, methyl methacrylate, methacrylic acid, ethyl acrylate and hydroxyethyl methacrylate. DynamX® H2O from Akzo Nobel is blend of an acrylates copolymer and a polyurethane polymer i.e. polyurethane-14/AMP-acrylates copolymer blend. Balance® CR from Akzo Nobel is an acrylates copolymer of two or more monomers of (meth)acrylic acid or one of their simple esters. In an embodiment, hairstyling formulation comprises two of more different hairstyling polymers, wherein the hairstyling polymer is selected from the group consisting of: acrylates copolymers of two or more monomers of (meth)acrylic acid or one of their simple esters; acrylates/hydroxyesters acrylates copolymers of butyl acrylate, methyl methacrylate, methacrylic acid, ethyl acrylate and hydroxyethyl methacrylate; polyurethane-14/AMP-acrylates polymer blend; and mixtures thereof. In an embodiment, hairstyling formulation comprises all three of hairstyling polymers listed above. In an embodiment, the product is substantially free of octylacrylamide/acrylate/butylaminoethyl methacrylate copolymers. Amphomer® is an octylacrylamide/acrylate/butylaminoethyl methacrylate copolymer.

In an embodiment, the hairstyling formulation comprises from about 3% to about 20% of a sole hairstyling polymer, wherein the sole hairstyling polymer is selected from the group consisting of: acrylates copolymers of two or more monomers of (meth)acrylic acid or one of their simple esters; and acrylates/hydroxyesters acrylates copolymers of butyl acrylate, methyl methacrylate, methacrylic acid, ethyl acrylate and hydroxyethyl methacrylate. In an embodiment, the hairstyling formulation comprises from about 4% to about 7% of a hairstyling polymer being the sole hairstyling polymer and the hairstyling polymer being an acrylates copolymer of two or more monomers of (meth)acrylic acid or one of their simple esters. As used herein "sole hairstyling polymer" means that the hairstyling formulation comprises only one type of hairstyling polymer and other hairstyling polymers are not present, and wherein the other hairstyling polymers do not fall within the definition provided for the sole hairstyling polymer.

In an embodiment, the hairstyling formulation comprises a mixture of hairstyling polymers. The mixture may comprise a hard hairstyling polymer and a soft hairstyling polymer. As used herein "hard hairstyling polymer" is a hairstyling polymer which provides excellent hairstyle hold and this hairstyle hold is more pronounced as the concentration of the hard hairstyling polymer in the hairstyling formulation increases. However, high concentrations of hard hairstyling polymer typically have negative effect on the hair feel i.e. consumers find the palpable feel of the hair unacceptable e.g. rough. As used herein "soft hairstyling polymer" is a hairstyling polymer which provides excellent i.e. natural hair feel, particularly soft and/or smooth hair feel, but typically the hairstyle hold provided is limited.

In an embodiment, the hairstyling formulation comprises from about 3% to about 20% of a sole hairstyling polymer, wherein the sole hairstyling polymer is a hard hairstyling polymer.

The softness and hardness of the hairstyling polymer depends on the M. Wt. and the glass transition temperature of the hairstyling polymer, and also the chemistry of the hairstyling polymer i.e. the chemistry of the monomers.

In an embodiment, the hard hairstyling polymer has a glass transition temperature of greater than or equal to 10° C. and the soft hairstyling polymer has a glass transition temperature of less than 10° C. "Glass transition temperature" or "$T_g$", as used herein, means the lowest temperature at which a polymer can be considered flowable, which means the polymer chains can slide past each other when a force is applied. The $T_g$ as used herein may be measured according to DIN EN 61 006.

In an embodiment, the M. Wt. of the hairstyling polymer(s) is from about 10 thousand g/mol to about 200 thousand g/mol, or from about 20 thousand g/mol to about 150 thousand g/mol. In an embodiment, the hard hairstyling polymer has M. Wt. of from about 90 thousand g/mol to about 200 thousand g/mol. In an embodiment, the soft hairstyling polymer has M. Wt. of from about 10 thousand g/mol to about 90 thousand g/mol.

The hairstyle hold provided by increasing amounts of the soft hairstyling polymer in the hairstyling formulation increases, but then plateaus. In other words, the soft hairstyling polymer has a maximum hairstyle hold that it can provide. Consequently, it can be advantageous to provide a mixture of a hard hairstyling polymer and a soft hairstyling polymer.

In an embodiment, the hard hairstyling polymer is selected from the group consisting of: acrylates copolymers of two or more monomers of (meth)acrylic acid or one of their simple esters; acrylates/hydroxyesters acrylates copolymers of butyl acrylate, methyl methacrylate, methacrylic acid, ethyl acrylate and hydroxyethyl methacrylate; and mixtures thereof. In an embodiment, the soft hairstyling polymer is selected from the group consisting of: a polyurethane-14/AMP-acrylates polymer blend; latex hairstyling polymers; polyesters; and mixtures thereof. In an embodiment, the soft hairstyling polymer is a polyurethane-14/AMP-acrylates polymer blend or a latex hairstyling polymer. In an embodiment, the soft hairstyling polymer is a polyurethane polymer. The polyurethane polymer may be a polyurethane-14/AMP-acrylates polymer blend. In an embodiment, the hairstyling formulation comprises an additional soft hairstyling polymer, wherein the additional soft hairstyling polymer is selected from the group consisting of: PVP (polyvinylpyrrolidone) polymers; PVP-VA-copolymers (vinylpyrrolidone/vinylacetate copolymers); polyesters; and mixtures thereof.

In an embodiment, the hairstyling formulation comprises a mixture of: a soft hairstyling polymer being a polyurethane-14/AMP-acrylates polymer blend or a latex hairstyling polymer; and a hard hairstyling polymer selected from the group consisting of: acrylates copolymers of two or more monomers of (meth)acrylic acid or one of their simple esters; and acrylates/hydroxyesters acrylates copolymers of butyl acrylate, methyl methacrylate, methacrylic acid, ethyl acrylate and hydroxyethyl methacrylate. In an embodiment, the mixture is the combination of: a soft hairstyling polymer being a polyurethane-14/AMP-acrylates polymer blend or a latex hairstyling polymer; and both of the following two hard hairstyling polymers: acrylates copolymers of two or more monomers of (meth)acrylic acid or one of their simple esters; and acrylates/hydroxyesters acrylates copolymers of butyl acrylate, methyl methacrylate, methacrylic acid, ethyl acrylate and hydroxyethyl methacrylate. In an embodiment, the mixture comprises a polyester and an acrylates copolymers of two or more monomers of (meth)acrylic acid or one of their simple esters. In an embodiment, the polyester is a polyester-5 polymer. In an embodiment, the mixture comprises at least 2, or at least 3, different hairstyling polymers. An example of a polyester-5 polymer is AQ® 48 Ultra Polymer from Eastman Chemical Company.

In an embodiment, the weight ratio of hard hairstyling polymer to soft hairstyling polymer (hard:soft) in the mixture is from about 10:1 to about 1:10, or from about 10:1 to about 1:2. In an embodiment where the mixture comprises at least 2 different hairstyling polymers, or only 2 different hairstyling polymers, the weight ratio of hard:soft may be from about 10:0.5 to about 9:3, or about 10:1 to about 9:2. In an embodiment where the mixture comprises at least 3 different hairstyling polymers, or only 3 different hairstyling polymers, the weight ratio of hard:soft may be from about 10:1 to about 6:4, or about 10:2 to about 8:3.

In an embodiment, the hairstyling formulation further comprises an additional ingredient selected from the group consisting of: octylacrylamide/acrylate/butylaminoethyl methacrylate copolymers, panthenol compounds, silicone compounds, latex compounds, and mixtures thereof. In an embodiment, the hairstyling formulation further comprises a panthenol compound. In an embodiment, the panthenol compound is selected from the group consisting of: panthenol, a pantothenic acid derivative, and mixtures thereof. In an embodiment, the panthenol compound is selected from the group consisting of: D-panthenol ([R]-2,4-dihydroxy-N-[3-hydroxypropyl)]-3,3-dimethylbutamide), D/L-panthenol, pantothenic acids and their salts, panthenyl triacetate, royal jelly, panthetine, pantotheine, panthenyl ethyl ether, pangamic acid, pantoyl lactose, Vitamin B complex, and mixtures thereof. In an embodiment, the hairstyling formulation comprises a mixture comprising a hard hairstyling polymer, panthenol, and optionally a soft hairstyling polymer. In an embodiment, the hairstyling formulation comprises panthenol. The panthenol compound is able to have a 'softening' effect on the hard hairstyling polymer. The hairstyling formulation may comprise from about 0.1% to about 0.6%, or from about 0.1% to about 0.3%, of a panthenol compound by total weight of the hairstyling formulation and the propellant. The weight ratio of hard hairstyling polymer to panthenol compound may be from about 100:6 to about 100:1, or from about 100:4 to about 100:20. In an embodiment, the panthenol compound is either D-panthenol or D/L-panthenol. In an embodiment, the hairstyling formulation further comprises a silicone compound. The silicone is useful because it gives a smoother feel and also shine to the hair. In an embodiment, the silicone compound is a dimethicone compound. In an embodiment, the silicone compound is a PEG dimethicone, for example PEG-12 dimethicone. In an embodiment, the hairstyling formulation further comprises a octylacrylamide/acrylate/butylaminoethyl methacrylate copolymer. Amphomer® is an octylacrylamide/acrylate/butylaminoethyl methacrylate copolymer.

In an embodiment, the hairstyling polymer is a water-compatible hairstyling polymer, alternatively a water-soluble hairstyling polymer. In an embodiment, the hairstyling formulation is substantially free from a water-incompatible hairstyling polymer. Balance® CR, Acudyne™ 1000, DynamX® H2O from Akzo Nobel are water-compatible.

In an embodiment, the hairstyling formulation further comprises a latex hairstyling polymer. In an embodiment, the latex hairstyling polymer is a polyurethane polymer and/or an aqueous polyurethane dispersion. In an embodiment, the polyurethane polymer is Polyurethane-48. Baycusan® C 1008 is a Polyurethane-48, which is an aqueous polyurethane dispersion.

In an embodiment, the product comprises less than about 0.5% of a cationic surfactant by total weight of the hairstyling formulation and propellant. In an embodiment, the hairstyling formulation comprises a polyurethane polymer and the hairstyling formulation is substantially free of a cationic surfactant. In an embodiment, the sole hairstyling polymer is neither a latex hairstyling polymer nor a polyurethane polymer. In an embodiment, the hairstyling formulation is substantially free of a polyurethane polymer. This is because, in certain circumstances, polyurethane polymers can cause residues on the hair after the ejected formulation has dried on the hair. Such residues are unsightly and not preferred by consumers since they can be confused with dandruff.

The tackiness on hands and/or hair of the present invention is lower than achieved by conventional ethanol-based aerosol hairsprays. In an embodiment, the product comprises from about 20% to about 50% VOC, by total weight of the hairstyling formulation and the propellant and the liquefied gas propellant is DME. The low tackiness on hands and/or hair benefit is also achieved for this embodiment.

Amphoteric polymers as well as anionic polymers such as Balance® CR are normally present in their neutralized or partially neutralized form. In an embodiment, the hairstyling polymer is at least 60%, or at least 80% neutralized.

Suitable neutralisers include potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia ($NH_3$), triethanolamine, trimethylamine (Tris Amino Ultra), aminomethylpropandiol (AMPD). In an embodiment, the neutralising agent is 2-aminobutanol, ammonia, or 2-aminomethyl propanol.

The hairstyling formulation may further comprise a surfactant. The hairstyling formulation may comprise 1% or less surfactant, or 0.6% or less, or 0.4% or less, or 0.3% or less, by total weight of the hairstyling formulation and propellant. In an embodiment, the surfactant is selected from the group consisting of cationic surfactants, non-ionic surfactants, anionic surfactants, and mixtures thereof. Cationic surfactants may be selected from the group consisting of cetrimonium chloride (e.g. Quartamin 60L-G from Kao; DEHYQUART A-CA/DETEX; ARQUAD 16-25 LO); cocamidopropyl hydroxysultaine (e.g. REWOTERIC AM CAS); cocamidopropyl betaine (e.g. TEGO BETAIN F 50); betaine; and mixtures thereof. Non-ionic surfactants may be selected from the group consisting of: castor oil PEG-40 H (e.g. NEODOL 91-8); laureth-4 (e.g. DEHYDOL LS 4 DEO N); laureth-9; decyl glucoside (e.g. Plantacare 2000); polysorbate 20 (e.g. TWEEN 20 PHARMA from UNIQEMA); PEG-25 hydrogenated castor oil (e.g. SIMULSOL 1292 DF from SEPPIC); PEG-40 hydrogenated castor oil (e.g. CREMOPHOR CO 410 from BASF); PPG-1-PEG-9-laurylglycolether (e.g. Eumulgin L); siloxane polyalkyleneoxide copolymer (Silwet® L7604 from Momentive); and polydimethylsiloxane methylethoxylate (Silwet® L7600 from Momentive); and mixtures thereof. A suitable anionic surfactant is dioctyl sodium sulfosuccinate (DOSS or 1,4-dioctoxy-1,4-dioxobutane-2-sulfonic acid), an example of which is Aerosol OT-70 PG from Cytec. In an embodiment, the surfactant is selected from the group consisting of: castor oil PEG-40 H; cetrimonium chloride; laureth-4; laureth-9; decyl glucoside; cocamidopropyl hydroxysultaine; polysorbate 20; siloxane polyalkyleneoxide copolymer; dioctyl sodium sulfosuccinate; and mixtures thereof. In an embodiment, the surfactant is selected from the group consisting of: castor oil PEG-40 H; decyl glucoside; cocamidopropyl hydroxysultaine; polysorbate 20; siloxane polyalkyleneoxide copolymer; dioctyl sodium sulfosuccinate; and mixtures thereof. In an embodiment, the surfactant is selected from the group consisting of: siloxane polyalkyleneoxide copolymer; and dioctyl sodium sulfosuccinate; and mixtures thereof.

The hairstyling formulation comprises at least about 50%, or from about 50% to about 99%, or from about 60% to about 99%, or from about 70% to about 99% water by total weight of the hairstyling formulation and propellant. When the product is substantially free of VOC, the hairstyling formulation may comprise from about 90% to about 99% water, by total weight of the hairstyling formulation and propellant.

The product comprises about 2% or less alcohol by total weight of the hairstyling formulation and propellant. In an embodiment, the product comprises about 1.8% or less, or about 1.5% or less, or about 1% or less, alcohol by total weight of the hairstyling formulation and propellant, or is substantially free of alcohol. In an embodiment, the hairstyling formulation is substantially free of ethanol and propanol. In an embodiment, the product comprises about 5% or less, or 2% or less, or about 1.8% or less, or about 1.5% or less, or about 1% or less, aliphatic alcohol by total weight of the hairstyling formulation and propellant. "Aliphatic alcohol" as used herein means an alcohol comprising no aromatic group.

The hairstyling formulation may comprise at least one preservative. The preservative may be present in an amount of less than about 1.5%, or 0% to 1%, or 0.01% to 1% by total weight of the hairstyling formulation and propellant. Suitable preservatives include: phenoxyethanol (e.g. Euxyl® PE 9010), benzyl alcohol, propyleneglycol, PHMB (Poly-aminopropyl biguanide), Optiphen (Phenoxyethanol+caprylyl glycol) from ISP, Symtriol (1,2 octanediol and 1,2 hexanediol,Methylbenzyl alcohol) from Symrise, octylsalicylate, 1,3-bis(hydroxymethyl)-5,5-dimethylimidazolidine-2,4-dione (DMDM hydantoin; Nipaguard® DMDMH by Clariant), EDTA (Rexat), butylene glycol (Dekaben LMB), and parben types e.g. methylparaben (e.g. PHB-methyl ester from Schtitz & Co., or SLI Chemicals, or Nipagin® M), propylparaben (PHB-propylester from Solvadis Specialties).

The hairstyling formulation may further comprise at least one perfume or fragrance. The aerosol hairspray product may comprise a maximum of about 0.5% perfume or fragrance, or from about 0% to about 0.4%, or from about 0.03% to about 0.3%, by total weight of the hairstyling formulation and propellant.

The hairstyling formulation may further comprise vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their salts and/or derivatives, water insoluble amino acids such as tyrosine, tryptamine, viscosity modifiers, dyes, non-volatile solvents or diluents (water soluble and insoluble), pearlescent aids, foam boosters, additional surfactants or non-ionic cosurfactants, pediculocides, pH adjusting agents, perfumes, preservatives, chelants, proteins, skin active agents, sunscreens, UV absorbers, vitamins, niacinamide, caffeine and minoxidil. The product may comprise from about 0.01% to about 5% vitamins and/or amino acids, by total weight of the hairstyling formulation and propellant.

The aerosol hairspray product may further comprise pigment materials such as inorganic pigments, nitroso-, monoazo-, disazo-compounds, carotenoid, triphenyl methane, triaryl methane, chemicals of the quinoline, oxazine, azine, or anthraquinone type, as well as compounds which are indigoid, thionindigoid, quinacridone, phthalocianine, botanical, natural colors, and water-soluble components. The product may comprise from about 0.0001% to about 5% pigment materials, by total weight of the hairstyling formulation and propellant. The formulation(s) described herein may also contain antimicrobial agents which are useful as cosmetic biocides. The product may comprise from about 0.01% to about 5% antimicrobial agents, by total weight of the hairstyling formulation and propellant.

The hairstyling formulation may have a pH of from about 6 to about 10, or from about 7 to about 10, or from about 7 to about 9.

The product comprises a propellant, which is selected from the group consisting of compressed gas propellants, liquefied gas propellants, and mixtures thereof.

The product may comprise a compressed gas propellant. The compressed gas propellants may be selected from the group consisting of air, nitrogen ($N_2$), nitrous oxide ($N_2O$), carbon dioxide ($CO_2$), and mixtures thereof. In an embodiment, the compressed gas propellant is air or nitrogen ($N_2$). In an embodiment, the compressed gas propellant is nitrogen ($N_2$). In an embodiment, the compressed gas propellant is not carbon dioxide ($CO_2$)—particularly when a hairstyling polymer may precipitate due to effect of the $CO_2$ in lowering the pH of the hairstyling formulation. Also $CO_2$ typically permeates through plastic material to a greater or lesser extent i.e. 0% permeation is typically unachievable. The term "air" is defined herein as a gas comprising approximately 78% nitrogen, 21% oxygen, and 1% of carbon dioxide, argon and other trace elements. Since the content of air can vary, in an embodiment the compressed gas propellant is nitrogen gas. As defined herein, the compressed gases $N_2$, $CO_2$, and $N_2O$ are all non-flammable. $N_2O$ has a GWP of 298. When the propellant is air, a maximum of 1 g is utilised as propellant.

CFCs are not suitable propellants for the present invention due to their ozone depleting properties. For example, CFC-12 has a GWP of 10,900. In an embodiment, the product has a GWP of 100 or less, or 50 or less, or 20 or less, or 10 or less, or 5 or less.

The product may comprise a liquified gas propellant. The liquefied gas propellant may be selected from the group consisting of dimethylether (DME), 1,1-difluoroethane (HFC-152a), 1,1,1,2-tetrafluoroethane (HFC-134a), pentane, n-butane, iso-butane, propane, trans-1,3,3,3-tetrafluoropropene (HFO-1234ze), and mixtures thereof. In an embodiment, the liquefied gas propellant is dimethylether (DME) or 1,1-difluoroethane (HFC-152a). In an embodiment, the liquefied gas propellant is DME.

For the purposes of the present invention, all the liquified gas propellants mentioned above are VOCs. Furthermore, as defined herein, n-butane is flammable (MIR=1.15, GWP=4); iso-butane is flammable (MIR=1.23); propane is flammable (GWP=3.3, MIR=0.49); HFC-134a is non-flammable (GWP=about 1400, MIR=0.00); HFC-152a is flammable (GWP=about 120, MIR=0.02); HFO-1234ze is non-flammable (GWP=6, MIR=0.09); DME is flammable (GWP=1, MIR=0.81).

The product comprises 54% or less VOC by total weight of the hairstyling formulation and propellant. In an embodiment, the product comprises from about 20% to about 50%, or from about 25% to about 45%, or from about 35% to about 42%, VOC, by total weight of the hairstyling formulation and propellant. In another embodiment, the propellant is a liquefied gas propellant and the liquefied gas propellant is DME, and wherein product comprises from about 25% to about 45%, or from about 35% to about 42%, DME. In another embodiment, the product comprises less than 15% VOC, or is substantially free of VOC, by total weight of the hairstyling formulation and propellant. In another embodiment, the product comprises from about 1% to less than 15% of a VOC, by total weight of the hairstyling formulation and propellant. In an embodiment where the propellant is a compressed gas propellant, the product comprises less than 15% of a VOC, by total weight of the hairstyling formulation and propellant.

The present invention comprises a container comprising a container wall which encloses a reservoir for storing a hairstyling formulation and a propellant. In an embodiment, the container wall comprises predominantly plastic material. In an embodiment, the container wall comprises at least about 80% plastic material, or from about 85% to about 100%, by total weight of the container. The term "plastic" is defined herein as any polymeric material that is capable of being shaped or molded, with or without the application of heat, and then hardened into a desired form including, polymers, resins, and cellulose derivatives. Usually plastics are homo- or co-polymers of high M. Wt. Cosmetic products contained in plastic containers are known. Plastic is a particularly advantageous material for containing cosmetic products because a greater variety of specific container forms may be created. The utilisation of plastic material(s) for a hairspray container provides an excellent means to deliver ease-of-use benefits to the consumer. For example, it is very easy to provide tactile advantages e.g. grip features, contours, and these tactile advantages can be designed with a high degree of specificity and accuracy. Furthermore, a plastic container can easily be moulded in one piece. Sealed plastic containers have a lower explosion potential than metal containers because, upon application of excessive temperature for example, due to the more elastic nature of plastic compared to metal, the plastic material may expand at a weak point in the container, e.g. where the container wall is thinner. Gradually and eventually the expansion at this weak point allows the high-pressured containers to escape via the formation of a hole. Furthermore, aesthetic benefits can also be realised more easily when a plastic container is used, for example, a transparent and/or translucent container material could be employed, and in addition to many other aesthetic benefits. From an environmental perspective, utilisation of a container comprising predominantly plastic material has sustainability benefits and results in a reduced carbon footprint than alternative container materials. Plastic is also more easily recycled than metal.

In an embodiment, the plastic material is selected from the group consisting of polyolefins, polyesters, polyamide, polyvinylchloride, acrylic, polycarbonates, polyethylene naphthalate (PEN), polyethylene terephthalate (PET), polystyrene, polyurethane, and mixtures thereof. In an embodiment, the plastic material is selected from the group consisting of polyethylene terephthalate (PET), polyethylene napththalate (PEN), and mixtures thereof. Polyethylene napththalate is available from Hoechst Trevira GmbH & Co. KG, under the trademark Polyclear®, including Polyclear® N10, Polyclear® N90 and Polyclear® N100.

The container may comprise polymers made from components derived from renewable sources i.e. non-petroleum sources. As used herein the term "sustainable polymer" means polymers made from components e.g. monomers, derived from renewable sources. Examples of renewable, non-petroleum sources include plants and microorganisms. The renewable, non-petroleum plants sources may include sugar cane, beets, corn, potatoes, citrus fruit, and woody plants. For example, ethanol can be produced from sugarcane. The ethanol may then be converted into ethylene, which can be polymerized to form polyethylene (PE). The monomers from which polypropylene (PP), polyester, and polyethylene terephthalate (PET) are synthesized, may also be derived from renewable sources. Sustainable polymers may be synthesized from monomers derived from starch and/or cellulose, or by modification of the polymer itself. Cellulosics are thermoplastic resins manufactured by the chemical modification of cellulose.

These sustainable plastic materials may be used as 100% of the plastic material utilized for the container wall, or blended into the petroleum-derived plastic material at varying levels in order to vary performance and/or for economic reasons. Certain materials derived from plant sources may be biodegradable. Sustainable polymers exhibiting biodegradability include aliphatic polyesters such as polylactic acid (PLA), polyglycolic acid (PGA), polybutylene succinate (PBS) and copolymers thereof, aliphatic-aromatic polyesters such as Ecoflex® from BASF and Biomax® from DuPont, polyhydroxyalkanoate (PHA) and copolymers thereof. Thermoplastic starch (TPS) materials are also biodegradable, as are cellulosics. The incorporation of biodegradable sustainable polymers may be at 100% of the utilized plastic material or in blends with other materials, in order to control the speed or degree of biodegradation, or for economic reasons. The speed and degree of biodegradation must be compatible with the purpose and features of the present invention. Ecoflex® from BASF, for example, is a biodegradable plastic material that biodegrades in soil or compost. It is stable on shelf for one year. It is particularly suitable for bags and films.

Recycled plastic material can also be re-ground. This post-consumer regrind resin may also be suitable for the present invention either when blended with other resins or used as 100% of the plastic material utilised. Re-ground polyethylene at certain densities (r-HDPE, r-LLDPE, r-LDPE), reground polypropylene (r-PP), and reground polyethylene terephthalate (r-PET) may be suitable.

Filler materials may be blended into the plastic material. The advantages of the incorporation of filler materials into plastic material include: adjustment of physical properties of the plastic, such as mechanical strength, density and cooling time, and also economic reasons. In an embodiment, the filler is selected from the group consisting of: starches, fibres from renewable sources such as hemp, flax, coconut, wood, paper, bamboo, and also inorganic materials such as calcium carbonate, mica, and talc. In addition, gas fillers such as high pressure gas, foaming agents or microspheres may be added to the plastic material.

Plastic materials can be defined by their glass transition temperature (Tg) and/or M. Wt. When the container wall comprises at least about 80% plastic material, or from about 85% to about 100% plastic material, by total weight of the container, the wall thickness of the container wall may also be important. In an embodiment, the plastic material is PET, wherein the glass transition temperature of from about 70° C. to about 80° C., and wherein the wall thickness is from about 0.5 mm to about 3.2 mm. An example PET container comprises the following wall thicknesses: shoulder about 0.65 mm; sidewall about 0.50 mm; outside base about 1.09 mm; base pushup about 2.90 mm. The container may be moulded to create a specific ergonomic external form or contour, for example, hand-shaped contours. Said form facilitates effective and precise use of the hairspray product, for example by providing more grip or non-slip. Other tactile features may also be provided on the surface of the container, for example pimples. In an embodiment, the container is not cylindrical in shape. Furthermore the container may be provided with specific aesthetic features, such as colour combinations, and transparent or translucent portions. In an embodiment, at least 50% of the container wall is translucent, or transparent. When externally viewable, bag-on-valve systems are less favoured by consumers for aesthetic reasons.

In an embodiment, the container wall comprises predominantly metal material. In an embodiment, metal material is selected from the group consisting of aluminium, tin plated steel, and combinations thereof. In an embodiment, the container wall comprises at least about 80%, or from about 85% to about 100% metal material, by total weight of the container. In an embodiment, the container wall comprises at least about 80% metal material by total weight of the container, and wherein the metal material is selected from the group consisting of: aluminium, tin plated steel, and combinations thereof; and wherein the propellant is a liquefied gas propellant, and wherein the liquefied gas propellant is selected from the group consisting of DME, 1,1-difluoroethane, 1,1,1,2-tetrafluoroethane, pentane, n-butane, iso-butane, propane, trans-1,3,3,3-tetrafluoropropene, and mixtures thereof; or DME, 1,1-difluoroethane, and mixtures thereof. In an embodiment, the container wall comprises an inner surface, wherein the inner surface is coated with a corrosion inhibitor. In an embodiment, the corrosion inhibitor is a polyamide-imide laquer. A suitable corrosion inhibitor is HOBA 8460, supplied by HOBA Lacke und Farben GmbH.

In an embodiment, the propellant and hairstyling formulation may freely communicate with one another inside the reservoir. In an embodiment, the propellant and hairstyling formulation are stored in a single compartment. In an embodiment, the aerosol hairspray product does not comprise a bag-on-valve system, especially when a portion of the container wall is translucent, or transparent. In an embodiment, the reservoir comprises a plurality of compartments for storing the hairstyling formulation and the propellant. In an embodiment, the propellant and hairstyling formulation are not stored in separate compartments. In an embodiment, the reservoir does not comprise a plurality of compartments for storing the hairstyling formulation and the propellant.

The pressure inside the reservoir can be measured with a pressure gauge (GCAS #60001439). The pressure inside the reservoir may be from about 1 bar to about 16 bar at 50° C. When the propellant is a compressed gas, the pressure inside the container may be from about 6 bar to about 12 bar, or from about 8 bar to about 10 bar, or from about 9 bar, at 50° C. When the propellant is a liquefied gas, the pressure inside the container may be from about 1 bar to about 7 bar, or from about 3 bar to about 5 bar, at 50° C. In an embodiment, the reservoir comprises a maximum volume of 220 ml of hairstyling formulation and propellant.

The product comprises a spraying device attached to the container for dispensing the hairstyling formulation from the reservoir of the container. In an embodiment, the spraying device comprises a spray nozzle. In an embodiment, the spraying device comprises a sealing valve and an actuator. The sealing valve and actuator may or may not be made from plastic material. Valve and actuators are, for example, available from Seaquist Closures (Freyung, Germany), Aptar, Precision and Coster (Switzerland). U.S. Pat. No. 3,819,090 relates to a valve cup device for pressurized dispensing containers comprising a one-piece molded plastic body. U.S. Pat. No. 5,199,615A relates to an aerosol dispenser. A suitable spraying device when the propellant is a liquefied gas propellant is as follows: valve: Precision; stem: 0.010 inch; restricted tail piece: 0.050 inch; vapour phase housing: 0.020 inch; actuator: Kosmos 0.016 inch Wirbel; diptube: capillar 0.060 inch. Suitable spraying devices include NAZ DR 5113" and NAZ DR 5118 both from Aptar. The spray properties can be altered by utilising a vapour housing hole in the stem, which can help to make a wet spray drier by using more gas from the vapour phase. In an embodiment where the propellant is a liquefied gas propellant, the spraying device comprises a vapour housing hole.

In an embodiment, the spray nozzle is a spray nozzle 2 for dispensing a fluid comprising a first element 20, preferably a nozzle cup 20, and a second element 22, preferably a pin 22, said first and second element 20, 22 forming an assembly 80 comprising a fluid chamber 40, preferably a ring chamber, for receiving the fluid, at least one feeding channel 42 for feeding the fluid from the fluid chamber 40 radially inward into a swirl chamber 44 and an outlet channel 18 with an entrance end 54 facing the swirl chamber 44 and an exit end 56 for discharging the fluid to the environment 58 of the spray nozzle 2, characterized in that the outlet channel 18 tapers in the flow direction of the fluid and the degree of tapering is either constant in the flow direction, or the degree of tapering decreases in the flow direction.

In an embodiment, the exit end 56 has a maximum diameter ($d_{max}$) between about 0.1 mm and about 0.8 mm, preferably between about 0.1 mm and about 0.25 mm, more preferably between about 0.1 mm and about 0.2 mm, still more preferably between about 0.12 mm and about 0.15 mm.

In an embodiment, the inner face 62 of the outlet channel 18 includes an angle (β), said angle (β) varying between about 70° and about 130°, preferably between about 80° and about 120°, more preferably between about 80° and about 110°.

In an embodiment, the feeding channel 42 comprises a first section 48 and a second section 50 following the first section 48 in the flow direction and abutting the swirl chamber 44, the width (w1) of the first section 48 decreasing in the flow direction and the width (w2) of the second section 50 being constant or decreasing to a lesser extent in the flow direction.

In an embodiment, the length (l) of the second section 50 in the flow direction is equal to or smaller than the width (w2) of the second section 50 or/and the height (h) of the first or/and second section 48; 50 is decreasing in the flow direction or/and the width (w2) of the second section 50 is equal to the height (h) of the second section 50.

In an embodiment, the ratio of the diameter ($d_s$) of the swirl chamber 44 to the diameter ($d_{max}$) of the exit end 56 is about 2.5 to about 3.5.

In an embodiment, the ratio of the sum of the cross-sectional areas of the at least one feeding channel 42 at their exit end 46 to the cross-sectional area of the exit end 56 of the outlet channel 18 is between about 1.5 and about 2.7, preferably between about 1.7 and about 2.6.

In an embodiment, the bottom 26 of the first element 20 exerts a pretension against the flow direction of the fluid of about 0.5 N to about 1.5 N, preferably of about 1 N.

In an embodiment, the bottom 26 of the first element 20 is conical in longitudinal direction 6 forming with the second element 22 a contact area which is defined by the penetration of the second element 22 during the assembly, which generate pretension between the first element 20 and the second element 22 due slightly bending the bottom 26 of the first element 20 in longitudinal direction 4.

In an embodiment, one of the first and second element 20, 22 comprises an elastic portion, the elastic portion being elastically deformed by the other element 22, 20 when the elements 20, 22 are assembled, the protrusions 28 or/and the section of the first element 20 carrying the protrusions 28 preferably forming the elastic portion.

In an embodiment, the first element 20 and the second element 22 are connected via a flexible connecting piece 38, preferably a strip, the connecting piece 38 more preferably being integrally formed or molded with the first and second element 20, 22.

In an embodiment, an outlet layer 64 with a first hole 66, a channel layer 68 with a second hole 70 and slots 72 and an inlet layer 74 with holes 76 are provided, said layers 64, 68, 74 being sandwiched such that the first hole 66 forms the outlet channel 18, the second hole 70 forms the swirl chamber 44, the slots 72 form the feeding channels 42 and the holes 76 in the inlet layer 74 form inlet holes for feeding the fluid from the fluid chamber 40 into the feeding channels 42, the layers 64, 68, 74 preferably being separable from each other or/and each of the layers 64, 68, 74 preferably being replaceable.

In an embodiment, there is provided an overlapping area 78 between the inlet holes and the feeding channels 42, the size of the overlapping area 78 or/and the distance between the overlapping area 78 and the swirl chamber 44 preferably being adjustable, the inlet layer 74 and the channel layer 68 more preferably being moveable, most preferably rotatable, relative to each other in order to adjust the size of the overlapping area 78 or/and the distance between the overlapping area 78 and the swirl chamber 44.

In an embodiment, the spray nozzle 2 is made of a plastic material selected from the following list: polyoxymethylene, polypropylene, polyethylene, polystyrene, acrylonitrile butadiene styrene, silicone, polyamide, polyethylene terephthalate, an elastomer or mixtures thereof.

Another embodiment of the first aspect relates to an aerosol hairspray product for styling and/or shaping hair wherein the product comprises:

i. a container comprising a container wall which encloses a reservoir for storing a hairstyling formulation and a propellant;

ii. the hairstyling formulation comprising:
 (a) at least about 50% water by total weight of the hairstyling formulation and propellant; and
 (b) from about 0.01% to about 20% of a hairstyling polymer by total weight of the hairstyling formulation and propellant, wherein the hairstyling polymer is selected from the group consisting of: acrylates copolymers of two or more monomers of (meth) acrylic acid or one of their simple esters; acrylates/ hydroxyesters acrylates copolymers of butyl acrylate, methyl methacrylate, methacrylic acid, ethyl acrylate and hydroxyethyl methacrylate; a polyurethane/acrylates polymer blend; and mixtures thereof; and iii. a propellant, which is selected from the group consisting of compressed gas propellants, liquefied gas propellants, and mixtures thereof; and iv. a spraying device attached to the container for dispensing the hairstyling formulation from the reservoir of the container;

and wherein the product comprises about 2% or less alcohol by total weight of the hairstyling formulation and propellant, or is substantially free of alcohol;

wherein the product comprises 54% or less volatile organic compound by total weight of the hairstyling formulation and propellant. All the features of the first aspect described herein are applicable to this embodiment also.

In the second aspect, the invention relates to a method for styling hair comprising the steps of: (i) applying to hair an ejected composition, which is ejected by the product according to the present invention; (ii) drying the ejected composition on the hair. The method may also comprise a step preceding step (i) wherein a hairdo or hairstyle is created. The method may also comprise a step preceding step (ii) but after step (i) wherein a hairdo or hairstyle is created.

In the third aspect, the invention relates to the use of the product according to the present invention, for fixing and/or shaping a hairstyle. In an embodiment of the third aspect, the use comprises using the product according to the present invention for fixing a hairstyle following the creation of a hairstyle. Alternatively, the use comprises using the product according to the present invention for creating and shaping a hairstyle.

A fourth aspect relates to a kit comprising at least one aerosol hairspray product, as described herein, and a communication describing the use of the product. The kit may further comprise an item selected from the group consisting of a shampoo, conditioner, mousse, gel, a hairstyling tool, blow dryer, curling tongs, and straightening irons. The hairstyling tool may be selected from the group consisting of hair bands, hair fasteners, combs, and brushes.

A fifth aspect relates to a hairstyling formulation comprising at least 50% water and a mixture of hairstyling polymers, wherein the mixture comprises a hard hairstyling polymer and a soft hairstyling polymer. The hard hairstyling polymers and soft hairstyling polymers may be as per the first aspect described herein. The hairstyling formulation according to the fifth aspect may be useful for hairspray products including aerosols and pumps spray, and also mousses, gels, tonics and other forms of hairstyling formulation. In an embodiment of the fifth aspect, the invention relates to the herein-described hairstyling formulation in the context of a hair styling product other than an aerosol hairspray. For example, mousses, gels and lotions comprising this hairstyling formulation are also useful styling products. In an embodiment, the invention relates to a mousse, gel or lotion comprising a hairstyling formulation, wherein the hairstyling formulation comprises (a) at least about 50% water; and (b) from about 0.01% to about 20% of a hairstyling polymer, wherein the hairstyling polymer is selected from the group consisting of: acrylates copolymers of two or more monomers of (meth)acrylic acid or one of their simple esters; acrylates/hydroxyesters acrylates copolymers of butyl acrylate, methyl methacrylate, methacrylic acid, ethyl acrylate and hydroxyethyl methacrylate; polyurethane-14/AMP-acrylates polymer blend; and mixtures thereof; and wherein the mousse, gel or lotion comprises about 2% or less alcohol, or is substantially free of alcohol and the mousse, gel or lotion comprises 7% or less VOC. Mousse products typical comprise a propellant, such as those propellants described in detail herein. Many features of the first aspect described herein are applicable to this aspect also.

DETAILED DESCRIPTION OF THE DRAWINGS OF THE INVENTION

FIG. 1 to 4 show views of a first embodiment of the spray nozzle 2 for dispensing a fluid. In the figures, the opposing longitudinal directions 4, 6, the opposing radial directions 8, 10 and the opposing circumferential directions 12, 14 of the spray nozzle are indicated by corresponding arrows. The longitudinal axis 16 of the spray nozzle 2 extends in the longitudinal directions 4, 6, said longitudinal axis 16 further forming the centre axis of the outlet channel 18.

The spray nozzle 2 is assembled from a first element 20 and a second element 22 thereby forming an assembly 80. The first element 20 is a nozzle cup 20, i.e. having a cup-like structure with a first section 24 extending in the circumferential directions 12, 14 and forming a surrounding wall and a second section 26 forming the bottom 26. The second section 26 further comprises protrusions 28, said rib-like protrusions 28 extending in the longitudinal direction 6 and in the radial directions 8, 10. As can be best seen in FIG. 2, there are provided grooves 30 in the circumferential directions 12, 14 between the protrusions 28, said grooves being provided to form the feeding channels 42 as will be described later. The protrusions 28 comprise an upper surface serving as a support surface 32 for supporting the second element 22, said support surface 32 facing the second element 22. Further, the protrusions 28 comprise side surfaces 34 facing the grooves 30 and feeding channels 42, respectively.

The second element 22 may be a pin 22 basically having a cylindrical form with a front face 36, said front face 36 bulging out in the longitudinal direction 4. In this embodiment, the front face 36 has a form of a spherical cap. The second element 22 is inserted into the first element 20, so that the front face 36 is supported on the support surfaces 32 of the protrusions 28. In this connection it should be mentioned, that the second element 22 may also be formed by a ball, which is pressed or clipped into the first element 20. Independent of the chosen form of the second element 22, it is preferred if the second element 22 could be snapped or clicked into its place within the first element 20, even if corresponding notches, snaps or the like for providing a form-fit or/and a force-fit are not shown in the figures.

The first element 20 and the second element 22 may be connected via a flexible connecting piece 38, which—in this case—is formed by a strip. The connecting piece 38 is integrally formed or molded with the second element 22 and at least the first section 24 of the first element 20. Even the second section 26 of the first element 20 may be integrally formed or molded with the first section 24 of the first element 20 and consist of the same material. However, in this case the second section 26 has been subsequently fastened to the first section 24 since the second section 26 is made of a different material, as will be described hereinafter. Irrespective of the second section 26 being integrally formed with the first section 24 or not, the first element 20 comprises an elastic portion.

As already indicated above, the first element 20 is at least partially made of an elastic material being more elastic than the material of the second element 22. In this case, the second section 26 of the first element 20 with its protrusions 28 and its bottom section 26 carrying said protrusions 28 is made of the elastic material, said elastic material being more elastic than the material of the second element 22 and more elastic than the material of the first section 24 of the first element 20. Thus, the afore-mentioned elastic portion of the first element 20 is essentially formed of the protrusions 28 and its bottom section carrying said protrusions 28. The elastic portion of the first element 20 is elastically deformed by the second element 22 when the elements 20, 22 are assembled.

Further, the bottom 26, i.e. second section 26, of the first element 20 exerts a pretension against the flow direction of the fluid of about 0.5 N to about 1.5 N, preferably of about 1 N. In other words, during the assembly of the spray nozzle 2, i.e. when the second element 22 is inserted into the first element 20 a bending of the bottom 26 of the first element 20 to a flat position occurs, thereby generating that pretension against the second element 22. This pretension assures adhesion of the first element 20 to the second element 22 when fluid is dispensed at high pressure.

Even if the pre-assembled state is not shown, it is preferred if the bottom section carrying said protrusions 28 is curved or convex towards the second element 22 and in the longitudinal direction 6 before the first and second element 20, 22 are assembled.

In one example, the spray nozzle 2 is assembled by inserting the pin 22 into the nozzle cup 20 in the longitudinal direction 4 as shown in FIG. 1, thereby creating a fluid chamber 40, feeding channels 42 and a swirl chamber 44, while the outlet channel 18 is already provided in the second section 26 of the nozzle cup 20. The fluid chamber 40 is positioned in the radial directions 8, 10 between the first section 24 of the nozzle cup 20 and the pin 22, so that the fluid chamber 40 is formed as a ring chamber. The fluid chamber 40 receives the fluid to be dispensed from a fluid storage chamber or container, which is not shown in the drawings. In the longitudinal direction 4 the fluid chamber 40 abuts the radial outer ends of the feeding channels 42, so that there is a fluid connection between the fluid chamber 40 and the feeding channels 42.

Figure 2:
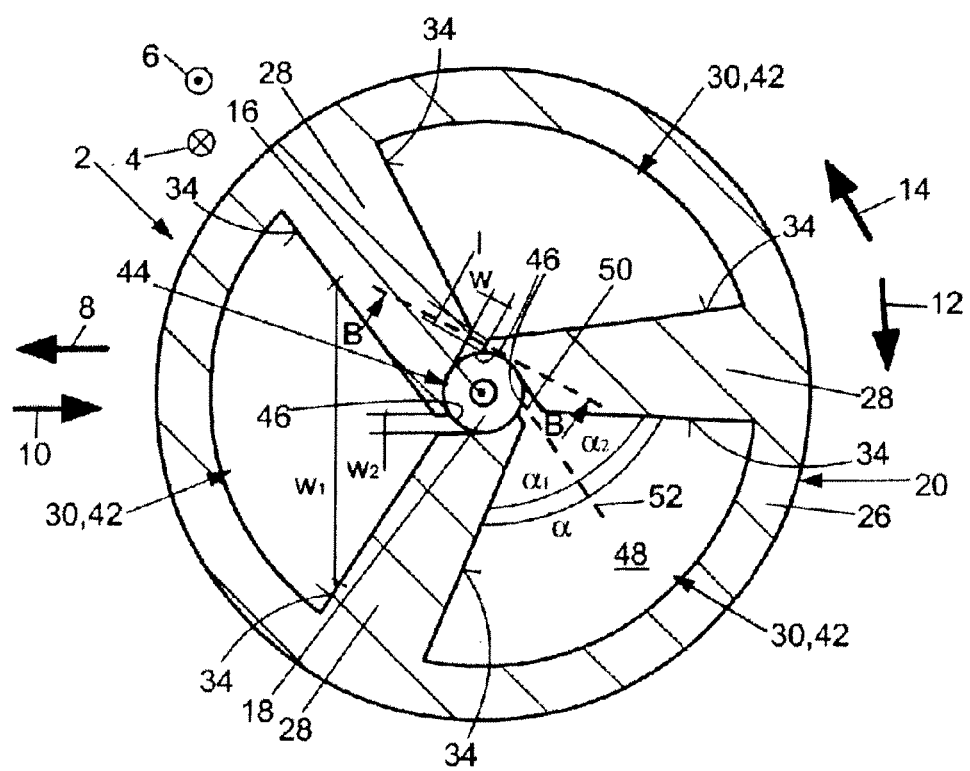
FIG. 2 shows a cross-sectional view along line A-A in FIG. 1.
Figure 3:
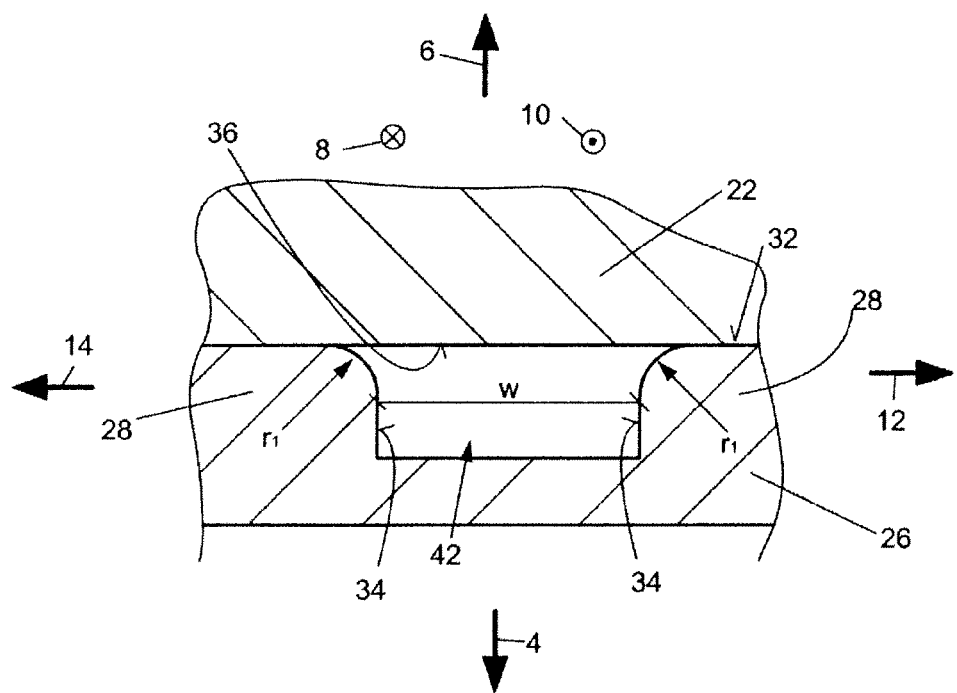
FIG. 3 shows a cross-sectional view along line B-B in FIG. 2.

As can especially be seen in FIG. 2, the feeding channels 42 are extending radially inward to an exit end 46 of the feeding channels 42, where the feeding channels 42 abut the swirl chamber 44, so that the fluid may be fed from the fluid chamber 40 via the feeding channels 42 into the swirl chamber 44. As shown in FIG. 3, the feeding channels 42 are limited in the circumferential directions 12, 14 by the side surfaces 34 of the protrusions 28, in the longitudinal direction 6 by the front face 36 of the second element 22, said second element 22 covering the grooves 30 to form the feeding channels 42, and in the longitudinal direction 4 by the bottom of the second section 26 carrying the protrusions 28.

In FIG. 2, the feeding channels 42 comprise a first section 48 abutting the fluid chamber 40 and a second section 50 following the first section 48 in the flow direction and radial direction 10, respectively. The second section 50 abuts the swirl chamber 44 with the exit end 46. As shown in FIG. 2, the width w1 of the first section 48 decreases in the flow direction and the radial direction 10. In contrast to this, the width w2 of the second section 50 is constant or decreases to a lesser extent than the first section 48 in the flow direction and radial direction 10.

The protrusions 28, which form the side walls of the first sections 48, include an angle α, between the protrusions' side walls as shown. In FIG. 2, there is further indicated a centerline 52 of the second section 50 extending in the radial directions 8, 10. Said centerline 52 subdivides the angle α into a first angle α1 and a second angle α2. The maximum difference between the first angle α1 and the second angle α2 is 10°, more preferably 5° or 1°, most preferably 00. Due to the bulged out front face 36 of the second element 22, the height h of the first section 48 or/and second section 50 of the feeding channels 42 decreases in the flow direction and the radial direction 10. Further, the length l of the second section 50 in the flow direction and the radial direction 10 is equal to or smaller than the width w2 of the second section 50. In addition, the width w2 of the second section 50 is equal to the height h of the second section 50.

As shown in FIG. 3, in the transition region between the support surfaces 32 and the side surfaces 34 the protrusions 28 comprise a radius r1. In order to have a compact cross-sectional form, the ratio of the radius r1 to the width w, e. g. w1 or w2, of the feeding channel 42 is equal to or less than ⅓, more preferably equal to or less than ¼, most preferably equal to or less than ⅕.

Even if the first element 20 and the second element 22 are assembled, they are still movable relative to each other into different relative positions. In the shown embodiment, the elements 20 and 22 may be moved in the longitudinal direction 4, 6 relative to each other. By this relative movement the form, dimensions or/and justification of the feeding channels 42 or/and the swirl chamber 44 is changed by elastically deforming the protrusions 28 or/and the bottom of second section 26 of the first element 20, i.e. by elastically deforming the elastic portion of the first element 20. In other words, it is easy to change the behavior of the spray nozzle 2. Further, there are provided means (not shown) for locking the elements 20, 22 in their different relative positions.

Figure 4:
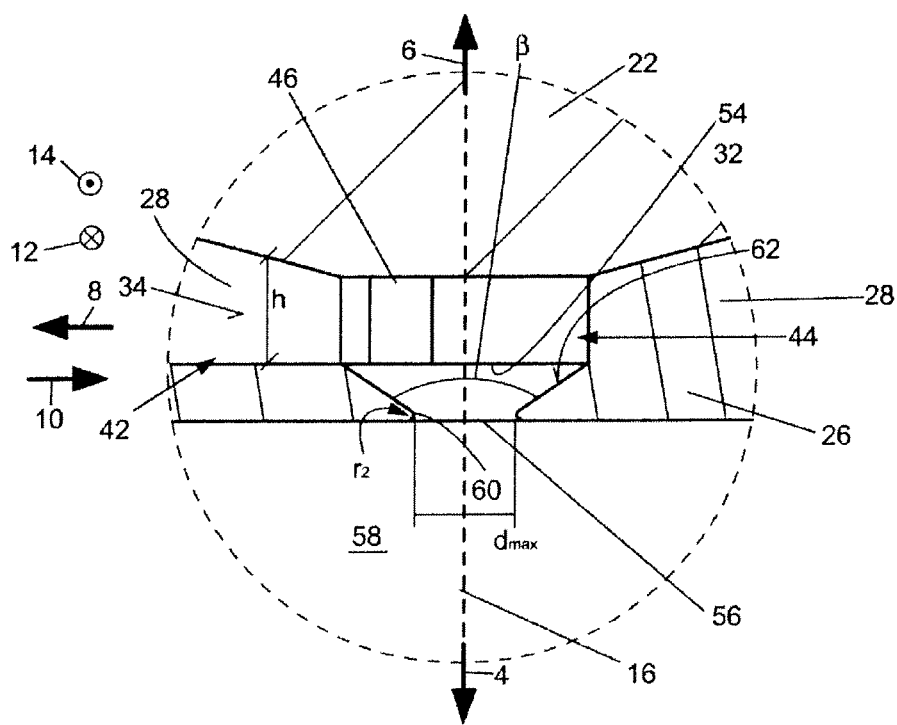
FIG. 4 shows the enlarged section A of FIG. 1.

With reference to FIG. 4, the afore-mentioned outlet channel 18 in the second section 26 of the first element 20 comprises an entrance end 54 facing the swirl chamber 44 in the longitudinal direction 6 and an exit end 56 for discharging the fluid to the environment 58 of the spray nozzle 2 and the sprayer, respectively, in the longitudinal direction 4. The outlet channel 18 tapers steadily in the flow direction and the longitudinal direction 4. Thus, the outlet channel 18 comprises at least one tapering portion, i.e. the outlet channel 18 is tapered in at least part along the length of the outlet channel 18 toward the exit. The tapering may be continuous or in steps, and may be angled or curved. In the shown embodiment, the tapering portion abuts the exit end 56 as well as the entrance end 54 of the outlet channel 18, so that the whole outlet channel tapers in the flow direction. The edge 60 surrounding the exit end 56 has a radius $r_2$. The radius $r_2$ is smaller than 0.03 mm, preferably smaller than 0.02 mm.

Further, the exit end 56 has a maximum diameter between 0.12 mm and 0.15 mm and more preferably a diameter about 0.14 mm with a corresponding maximum cross-sectional area to achieve an average particle size by volume ($D_{50}$) with a flow rate higher than 0.24 g/s at 9 bar (for the fluid water is considered), which is equal or lower than 60 am, or preferably equal or lower than 50 am, or more preferably equal or lower than 45 μm. This diameter further achieves an average particle size by volume ($D_{32}$) which is equal or lower than 50 am, or preferably equal or lower than 45 am, or more preferably equal or lower than 40 am. The average percentage of particles having a diameter smaller than 10 μm (%<10 μm) is less than 2%, preferably less than 1.5%, more preferably less than 1%.

A bigger geometry of the nozzle having a diameter ($d_{max}$) about 0.8 mm and, thus, providing a higher flow rate, e.g. higher than 3.2 g/s at 2 bar, achieves an average particle size by volume ($D_{50}$) (for the fluid water is considered) which is equal or lower than 120 lam, or preferably equal or lower than 115 μm. This diameter further achieves an average particle size by volume ($D_{32}$) which is equal or lower than 100 am, or preferably equal or lower than 96 am. The average percentage of particles having a diameter smaller than 10 μm (%<10 μm) is less than 1.5%, preferably less than 1%, more preferably less than 0.5%.

Above this, the outlet channel 18 has an inner face 62 surrounding the outlet channel 18 and limiting the same in the radial direction 8. The inner face 62 of the outlet channel 18 includes an angle β, said angle β preferably varying between 70° and 130°, preferably between 80° and 120°, more preferably between 80° and 110°.

As shown in FIG. 4, the degree of tapering of the outlet channel 18 is constant in the flow direction and the longitudinal direction 4. In the shown embodiment this is achieved by at least a tapering portion of the outlet channel 18 or the whole outlet channel 18 having the form of a truncated cone or a truncated pyramid. It has further been found out, that the pressure drop, i.e. energy dissipation in the spray nozzle 2 could be reduced and a further reduction of the minimum pump pressure for dispensing the fluid could be achieved by adjusting the ratio of the sum of the cross-sectional areas of the feeding channels 42 at their exit end 46 to the cross-sectional area of the exit end 56 of the outlet channel 18. This ratio is between about 1.5 and about 2.7, preferably between about 1.7 and about 2.6. Further, the ratio of the diameter $d_s$ of the swirl chamber 44 to the diameter $d_{max}$ of the exit end 56 of the outlet channel 18 is about 2.5 to about 3.5.

Figure 5:
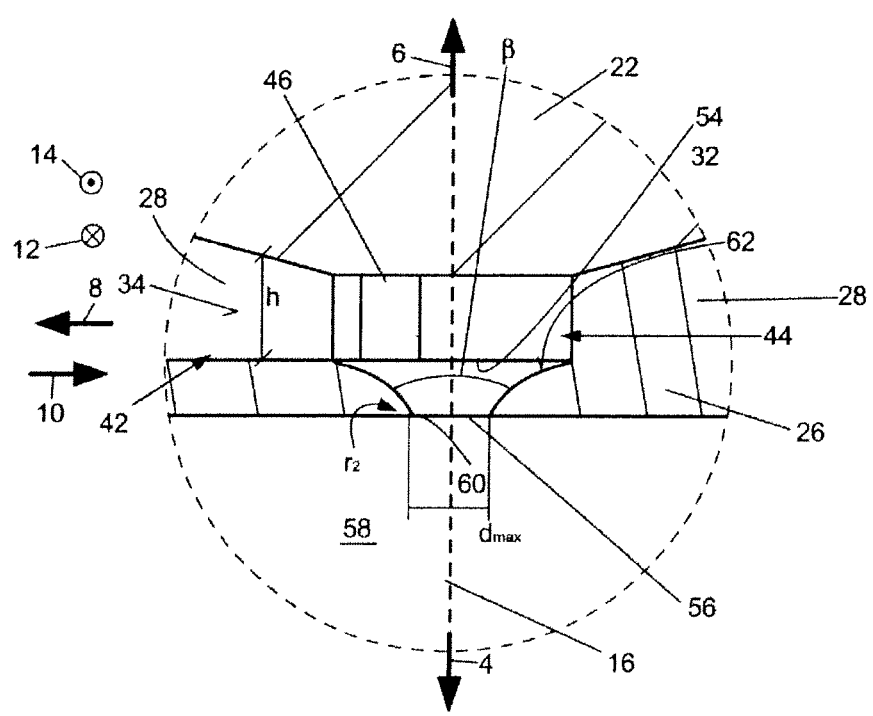
FIG. 5 shows the enlarged section A of FIG. 1 with a modification.

FIG. 5 shows the enlarged section A of FIG. 1 with a first modification. In the following only the differences will be described, the same reference signs will be used for similar or the same components and the above description of the first embodiment applies accordingly in this regard.

In contrast to the outlet channel 18 described with reference to FIG. 1 to 4, the degree of tapering of outlet channel 18 according to FIG. 5 decreases in the flow direction and the longitudinal direction 4. This is achieved by providing an inner face 62 of the outlet channel 18 being curved in the flow direction and the longitudinal direction 4. In the embodiment according to FIG. 5, at least a tapering portion of the outlet channel 18 or the whole outlet channel 18 has the form of a truncated hyperboloid of revolution.

Figure 6:
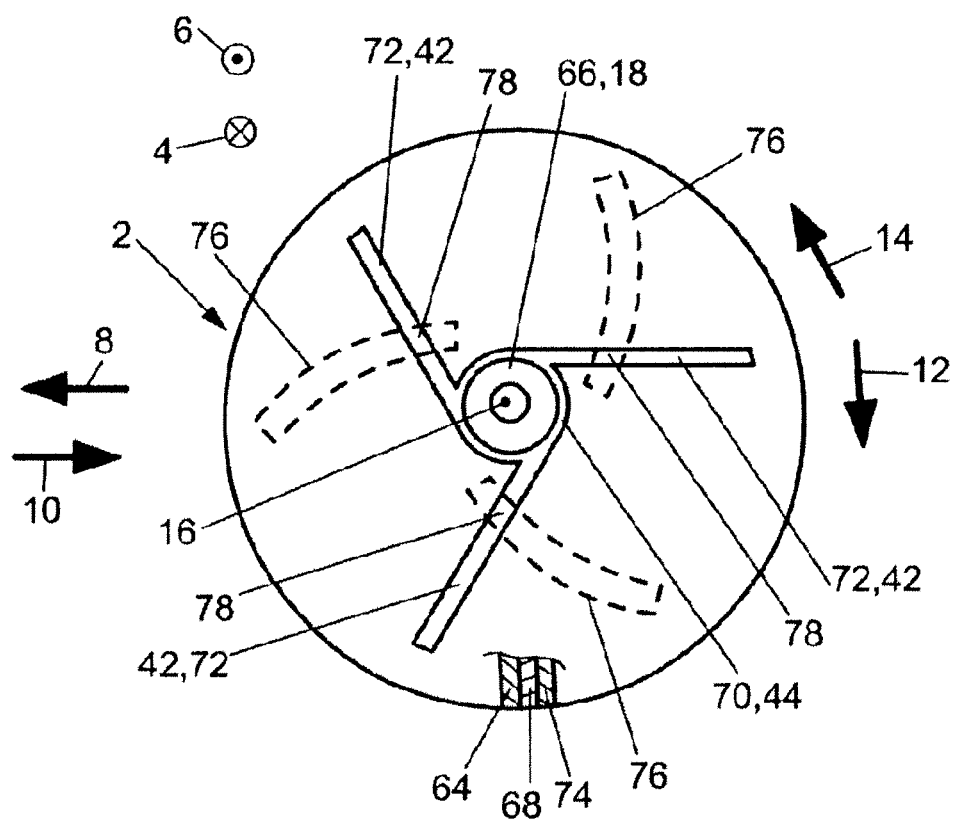
FIG. 6 shows a schematic view of an embodiment of the spray nozzle.

FIG. 6 shows a second embodiment of the spray nozzle according to the invention. Since the second embodiment at least partially corresponds to the first embodiment according to FIG. 1 to 5, in the following only the differences will be described, the same reference signs will be used for similar or the same components and the above description of the first embodiment applies accordingly in this regard.

The spray nozzle 2 according to FIG. 6 comprises at least three layers, i.e. an outlet layer 64 with a first hole 66, a channel layer 68 with a second hole 70 and slots 72 and an inlet layer 74 with slot-like holes 76, said layers 64, 68 and 74 being sandwiched, while the inlet layer 74 is shown in a transparent manner in FIG. 6 to increase the intelligibility of the drawing. Being sandwiched this way, the first hole 66 forms the outlet channel 18, the second hole 70 forms the swirl chamber 44, the slots 72 form the feeding channels 42 and the holes 76 in the inlet layer form inlet holes for feeding the fluid from the fluid chamber 40 into the feeding channels 42. In the shown embodiment, the layers 64, 68 and 74 are separable from each other and each of the layers 64, 68 and 74 could be replaced, so that the layers 64, 68 and 74 could also be regarded as separate discs with corresponding slots and holes.

As shown in FIG. 6, there is provided an overlapping area 78 between the inlet holes 76 and the feeding channels 42 when viewed in the longitudinal direction 4. The inlet layer 74 and the channel layer 68 are moveable—in this case rotatable around the longitudinal axis 16—relative to each other, while the inlet holes 76 and the feeding channels 42 are formed such that, the distance between the overlapping area 78 and the swirl chamber 44 could be reduced by rotating the inlet layer 74 relative to the channel layer 68 in the circumferential direction 14 and could be enlarged by rotating the inlet layer 74 relative to the channel layer 68 in the circumferential direction 12. Thus, the distance between the overlapping area 78 and the swirl chamber 44 is adjustable.

Figure 7:
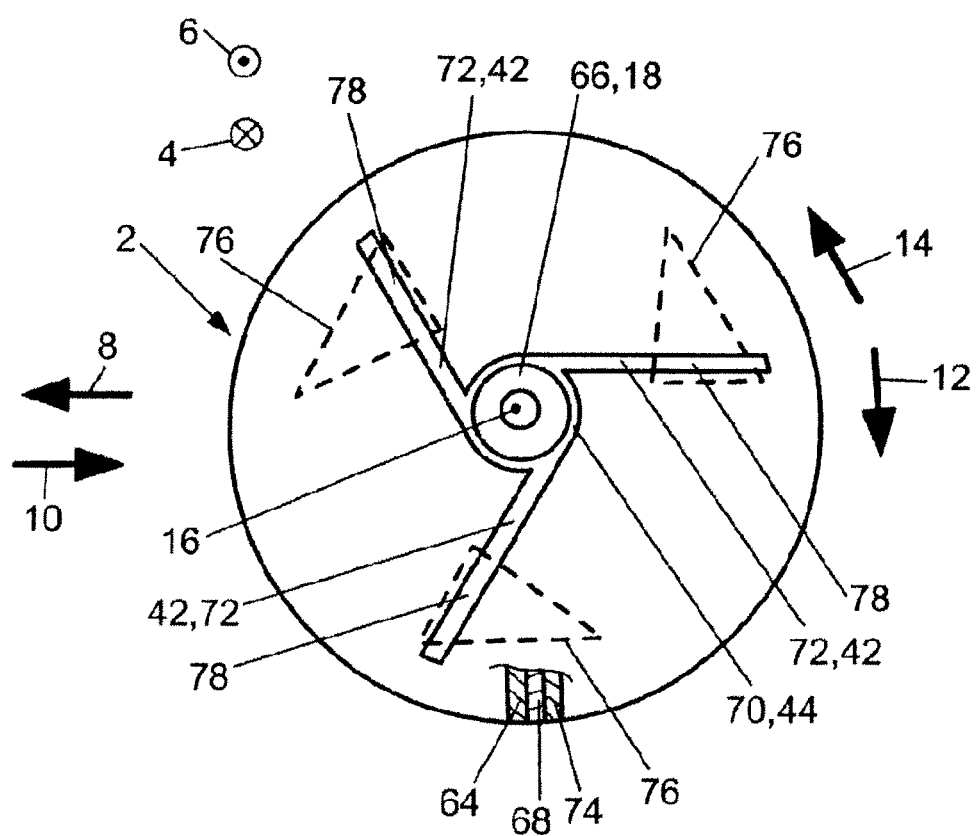
FIG. 7 shows a schematic view of an embodiment of the spray nozzle.

FIG. 7 shows a third embodiment of the spray nozzle 2 according to the invention. Since the third embodiment at least partially corresponds to the second embodiment according to FIG. 6, in the following only the differences will be described, the same reference signs will be used for similar or the same components and the above description of the first and second embodiment applies accordingly in this regard.

In contrast to the second embodiment, the inlet holes 76 and the feeding channels 42 of the third embodiment are formed such that, the size of the overlapping area 78 could be reduced by rotating the inlet layer 74 relative to the channel layer 68 in the circumferential direction 12 and could be enlarged by rotating the inlet layer 74 relative to the channel layer 68 in the circumferential direction 14. Thus, the size of the overlapping area 78 is adjustable.

It should be mentioned that the principles of the second and third embodiment could also be advantageously combined in a single spray nozzle 2, so that the size of the overlapping area 78 as well as the distance between the overlapping area 78 and the swirl chamber 44 could be adjusted by a relative movement between the inlet layer 74 and the channel layer 68.

The spray nozzle 2 is made of a plastic material, e.g. polyoxymethylene, polypropylene, polyethylene, polystyrene, acrylonitrile butadiene styrene, silicone, polyamide, polyethylene terephthalate or mixtures thereof. Further, the spray nozzle can additionally comprise an elastomer.

According to the invention, the spray nozzle 2 should be used in a sprayer, said sprayer preferably being a hand operated sprayer, for example a trigger sprayer, the sprayer more preferably comprising a fluid container being manually squeezable, a sprayer with a pressurized fluid storage container or a manually actuable pumping device, or in an electrically driven sprayer.

Pin bending and compression are problems that occur during the manufacturing process of spray nozzles having an exit end with a diameter ($d_{max}$) smaller than 0.25 mm, in particular smaller than 0.2 mm and even smaller than 0.15 mm. Therefore, high precision is required during the assembly of the pin 22 and nozzle cup 20. Thus, the spray nozzle 2 is produced by a precise injection molding process. In order to form the nozzle cup 20, the pin 22 (molding tool) is centered in a counter tool by an autopositioning process. The tapering, i.e. conical shape of the pin 22 facilitates centering of the molding tool in the counter tool as compared to a nozzle having a cylindrical pin. In addition, a conical molding tool (pin) is more robust than a cylindrical one. Further, in order to provide an edge surrounding the exit end 56 with a radius being smaller than 0.03 mm, preferably smaller than 0.02 mm, micro erosion is applied for the tool manufacturing.

Method of Making a Hairspray

First two solutions are made: a main mix and a second mix. The main mix comprises the hairstyling polymer(s), which are dissolved with stirring in water and components of the preservative system. A second mix is created which comprises water and the paraben-based preservative component(s) (e.g. methyl paraben). Optionally the second mix is heated up in a microwave to 90 to 95° C. in order to dissolve the paraben. The two mixes are then combined to create the hairstyling formulation. The hairstyling formulation is then put into the container and then container is sealed by crimping on a sealing mounting cup which includes a valve system. Then the propellant is added under pressure and then the spray nozzle is added to the container.

Examples

| Examples | 1 | 2 | 3 | 4 | 5 | 6 | 7 | 8 |
|---|---|---|---|---|---|---|---|---|
| Acrylates/hydroxyesters acrylates copolymer [1] | 6.7 | 5.5 | 3.6 | — | 3.35 | — | — | 0.2 |
| Polyurethane- 14/AMP-acrylates polymer blend [2] | — | — | 3.0 | 10.0 | 6.0 | 10.0 | — | 6.0 |

-continued

| | | | | | | | | |
|---|---|---|---|---|---|---|---|---|
| Acrylates Copolymer [3] | — | — | — | 5.6 | — | 1.7 | 4.1 | 1.0 |
| 2-Aminopropanol (AMP) | 0.6 | 0.25 | 0.17 | 0.35 | 0.15 | 0.2 | 0.3 | 0.25 |
| Castor oil PEG-40 H, (90%) | 0.1 | 0.2 | 0.15 | 0.3 | 0.3 | 0.3 | 0.2 | 0.15 |
| Disodium EDTA | 0.15 | 0.15 | 0.15 | 0.15 | 0.15 | 0.15 | 0.15 | 0.15 |
| Perfume | 0.2 | 0.07 | 0.3 | 0.15 | 0.1 | 0.05 | 0.1 | 0.15 |
| Phenoxyethanol [4] | 0.3 | 0.2 | 0.3 | 0.3 | 0.4 | 0.2 | 0.2 | 0.2 |
| 1,3-bis(hydroxymethyl)-5,5-dimethylimidazolidine-2,4-dione [5] | — | 0.1 | 0.2 | 0.4 | 0.2 | 0.3 | 0.4 | 0.3 |
| Methylparaben [6] | 0.2 | — | — | — | 0.2 | 0.2 | 0.2 | 0.2 |
| Deionised water | Add to 100 | Add to 100 | Add to 100 | Add to 100 | Add to 100 | Add to 100 | Add to 100 | Add to 100 |

| Examples | 9 | 10 | 11 | 12 | 13 | 14 | 15 | 16 |
|---|---|---|---|---|---|---|---|---|
| Acrylates/hydroxyesters acrylates copolymer [1] | 4.69 | 4.8 | 4.0 | — | — | 2.0 | 3.6 | — |
| Polyurethane- 14/AMP-acrylates polymer blend [2] | — | — | 7.0 | — | 7.0 | 6.0 | 7.0 | — |
| Acrylates Copolymer [3] | — | — | — | 5.1 | 3.9 | — | — | 6.5 |
| 2-Aminopropanol (AMP) | 0.42 | 0.49 | 0.4 | 0.38 | 0.25 | 0.21 | 0.37 | 0.53 |
| Castor oil PEG-40 H, (90%) | 0.1 | 0.2 | 0.3 | 0.3 | 0.1 | 0.3 | 0.2 | 0.3 |
| Disodium EDTA | 0.07 | — | — | — | 0.07 | 0.1 | 0.1 | 0.1 |
| Perfume | 0.07 | 0.1 | 0.07 | 0.15 | 0.05 | 0.035 | 0.03 | 0.08 |
| Phenoxyethanol [4] | 0.3 | 0.3 | 0.3 | 0.3 | 0.3 | 0.3 | 0.3 | 0.3 |
| 1,3-bis(hydroxymethyl)-5,5-dimethylimidazolidine-2,4-dione [5] | — | 0.29 | 0.29 | 0.29 | — | 0.29 | 0.29 | 0.29 |
| Methylparaben [6] | 0.1 | — | — | — | 0.1 | 0.14 | 0.14 | 0.2 |
| Ethanol | — | — | — | 1 | — | — | — | — |
| DME | 30 | 30 | 30 | 28 | 30 | 30 | 30 | 40 |
| Deionised water | Add to 100 | Add to 100 | Add to 100 | Add to 100 | Add to 100 | Add to 100 | Add to 100 | Add to 100 |

Key:
[1] = Acudyne ® 1000 (45% solution);
[2] = DynamX H$_2$O ® (25% solution);
[3] = Balance ® CR (45% solution);
[4] = Euxyl ® PE 9010;
[5] = Nipaguard ® DMDMH;
[6] = PHB-methylester from Schütz.

Any of examples 1 to 8 may be placed in a predominantly plastic or predominantly metal container. The propellant may be a compressed gas propellant such that the product comprises 15% or less VOC by total weight of the hairstyling formulation and propellant. The spraying device may comprise the spray nozzle of claim 8.

Any of examples 9 to 16 may be placed in container wherein the container wall comprises at least about 80% metal material by total weight of the container. The metal material may be selected from the group consisting of: aluminium, tin plated steel, and combinations thereof. The propellant is DME as stated in the table.

Performance Data

Experiment 1—Sensory Data

Aerosol hairspray products pursuant to the present invention comprising hairstyling formulations selected from the above example section were compared with a standard aerosol hairstyling product with excellent performance. The standard aerosol hairspray product comprises: 50% DME propellant, the container is a metal container, a hairspray formulation comprising 3% Amphomer as hairstyling polymer, circa 38% ethanol, and less than 1% water; and wherein the product comprises VOC 95% (these percentages are by total weight of the hairstyling formulation and propellant).

The ejected compositions from these products are sprayed onto hair and compared for sensory criteria. When the difference between the product pursuant to the present invention and the standard product is from −1 to +1 (i.e. one point better or worse), then an equals sign (=) is marked. When the difference is less than −1 or greater than +1 then a − or a + is marked, respectively. When the difference is greater than +2, then a ++ is marked.

| Criteria | Hairstyling formulation of Ex. 4 | Hairstyling formulation of Ex. 9 | Hairstyling formulation of Ex. 13 |
|---|---|---|---|
| Spraying device | Comprises the spray nozzle of claim 8. | Comprises a vapour housing hole. | Comprises a vapour housing hole. |
| Approx. VOC (%) | <1 | 30 | 30 |
| Propellant | Nitrogen | DME | DME |
| Total hairstyling polymer amount (%) | 5 | 3 | 5 |
| INITIAL HOLD [1] | = | = | = |
| DRYING TIME [2] | = | = | = |
| FEEL [3] | ++ | ++ | ++ |
| LOOK [4] | = | = | = |
| LOOK [5] | = | = | = |
| FEEL [6] | = | = | = |
| FEEL [7] | = | = | = |

Key:
[1] = Hold on mannequin (least hold to most hold);
[2] = Humidity after application (hair feels very dry to hair feels very wet);
[3] = Stickiness of hands/hair (not sticky at all to very sticky);
[4] = Hair look mannequin (very natural to very clumped);
[5] = Residues on mannequin hair (no residues at all to lots of residues);
[6] = Hair feel of mannequin after combing (very rough to very smooth);
[7] = Drawing fingers through hair of mannequin (hair clumped together to hair free flowing).

Experiment 2—Technical Data

The setting and the hold conferred to a hairstyle by a composition can be determined by measuring, respectively, the 3-point bending force and the hold force factor. 3-point bending force methodology: 0.5 ml/g hairstyling formulation is applied to the hair tress and massaged in for 1 min. The hair tresses are then dried in a drying cabinet for 45 min at 45° C. The tresses are then smoothed over by the fingers and dried overnight in a chamber at 20° C. at 65% relative humidity. The measurement is made with stamp at 5 positions on the sample. The 3-point bending force is measured according to the methodology detailed in F. Frosch, F. Vogel, 6th International Hair Science Symposium Of the German Wool Research Institute, Luneburg/Germany (1988). See also the methodology DIN-EN-658-5 from the American National Standards Institute. A mean value is calculated after 9 repeats are performed (i.e. n=9).

Hold force factor (also known as curl retention) methodology: 0.5 ml/g hairstyling formulation is applied to the hair tress and massaged in for 1 min. Each hair tress is then adjusted to 50% by weight of the hair tress and combed three times. The tresses are plaited and dried in a drying cabinet for 45 min at 45° C. The tresses are then dried overnight in a climatic chamber at 20° C. at 65% relative humidity. The curl retention measurements are taken the following day. The climatic conditions are: 20° C. at 85% relative humidity. The reading times are: after 0 h, 1 h, 2 h, 3 h 5 h and 24 h (h means hour). The hold force factor is measured according to the methodology detailed in C.R. Robbins, Chemical and Physical Behavior of Human Hair, 3rd edition, page 352, Springer-Verlag, New York (1994). A mean value is calculated after 3 repeats are performed (i.e. n=3).

Table X details the 3-point bending force and the hold factor after 1 h, 5 h and 24 h of the hairstyle, after applying the below-detailed hairstyling formulations. Where indicated, the hairstyling formulation is as per an example from the table in the examples section above. Samples A to D were treated with hairstyling formulations A to D, which comprise the indicated hairstyling polymer in deionised water. Total hairstyling polymer present is indicated in brackets. Samples α to γ (alpha to gamma) were control treatments as detailed below.

Conclusions from experiment 2 include: the samples left untreated exhibited the weakest (i.e. lowest) 3-point bending force and hold factor. PVP VA 64 and PVP K30 are softer hairstyling polymers, which, in the context of the hairstyling formulation pursuant to the present invention provide weaker hold as well as lower humidity resistance. The hard hairstyling polymers, especially the blends, show high humidity resistance—see hold factor values after 24 h in table X.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol hairspray product for styling and/or shaping hair wherein the product comprises:

TABLE X

| | Sample Hairstyling polymer [wt % of total hairstyling polymer] | | | | | | | | |
|---|---|---|---|---|---|---|---|---|---|
| Parameters | A [5] [3%] | B [2] [3%] | C [3] [3%] | D Mixture of [1] and [2] (1:1 ratio) [3%] | Ex. 1 [1] [3%] | Ex. 4 Mixture of [3] and [2] (1.1 ratio) [5%] | alpha (α) N/T | beta (β) [5] [3%] | gamma (γ) [6] [3%] |
| 3-point bending force (N) 1 break - hold | 2.101 +/− 0.413 | 2.48 +/− 0.60 | 3.02 +/− 0.70 | 2.216 +/− 0.449 | 2.231 +/− 0.358 | 3.211 +/− 0.796 | 0.09 +/− 0.01 | 1.82 +/− 0.62 | 1.95 +/− 0.628 |
| 3-point bending force (%) 3rd break - elasticity | 50.70 +/− 7.46 | 55.53 +/− 8.13 | 41.55 +/− 3.53 | 43.33 +/− 4.13 | 57.61 +/− 5.32 | 41.34 +/− 6.87 | 92.76 +/− 19.32 | 49.97 +/− 11.00 | 51.81 +/− 12.56 |
| Hold factor (%) after 0 h | 88.17 +/− 0.13 | 91.81 4 +/− 1.791 | 90.72 +/− 5.59 | 94.00 +/− 1.79 | 95.02 +/− 1.46 | 91.34 +/− 4.58 | 77.37 +/− 1.94 | 89.66 +/− 4.12 | 90.65 +/− 1.83 |
| Hold factor (%) after 1 h | 70.95 +/− 4.64 | 82.73 +/− 2.026 | 74.6 +/− 4.88 | 83.39 +/− 0.90 | 85.25 +/− 2.44 | 82.95 +/− 6.92 | 30.98 +/− 1.87 | 55.46 +/− 2.59 | 52.21 +/− 8.99 |
| Hold factor (%) after 5 h | 54.18 +/− 7.83 | 70.77 +/− 6.45 | 57.61 +/− 4.89 | 71.94 +/− 1.82 | 76.35 +/− 2.75 | 67.89 +/− 3.92 | 10.12 +/− 0.51 | 16.58 +/− 1.97 | 14.72 +/− 1.52 |
| Hold factor (%) after 24 h | 50.75 +/− 7.71 | 60.9 +/− 3.899 | 51.04 +/− 4.7 | 67.31 +/− 1.16 | 73.58 +/− 2.64 | 65.19 +/− 7.10 | 7.50 +/− 1.08 | 12.53 +/− 2.94 | 11.51 +/− 1.08 |

Key:
[1] = Acudyne ® 1000;
[2] = DynamX ® H2O;
[3] = Balance ® CR;
[4] = Amphomer ®;
N/T = not treated;
[5] = PVP/VA (vinylpyrrolidone/vinylacetate copolymer) 64;
[6] = PVP (polyvinylpyrrolidone) K30.

i. a container comprising a container wall which encloses a reservoir for storing a hairstyling formulation and a propellant;
ii. the hairstyling formulation comprising:
   (a) from ab out 50% to about 99% water by total weight of the hairstyling formulation and propellant;
   (b) from about 1% to about 16% of two neutralized hairstyling polymers by total weight of the hairstyling formulation and propellant, wherein the neutralized hairstyling polymers are selected from acrylates copolymer, acrylates/hydroxyesters acrylates copolymer, polyurethane-14/AMP-acrylates polymer blend,
   (c) a liquefied gas propellant;
   wherein the hair styling formulation is free of ethanol wherein the hairstyling formulation comprises less than 0.5% of a cationic surfactant by total weight of the hairstyling formulation and propellant;
iii. a spraying device attached to the container for dispensing the hairstyling formulation from the reservoir of the container.

2. The aerosol hairspray product of claim 1, wherein the hairstyling formulation comprises from about 25% to about 45% propellant, by total weight of the hairstyling formulation and propellant and wherein the propellant comprises dimethylether.

3. The aerosol hairspray product of claim 1, wherein the hairstyling formulation comprises a kinematic viscosity from about 1 $mm^2/s$ to about 15 $mm^2/s$, measured according to standard test DIN EN ISO 3104.

4. The aerosol hairspray product of claim 3, wherein the hairstyling formulation comprises a kinematic viscosity from about 1 $mm^2/s$ to about 10 $mm^2/s$, measured according to standard test DIN EN ISO 3104.

5. The aerosol hairspray product of claim 4, wherein the hairstyling formulation comprises a kinematic viscosity from about 1 $mm^2/s$ to about 4 $mm^2/s$, measured according to standard test DIN EN ISO 3104.

6. The aerosol hairspray product according to claim 1, comprising from about 3% to about 8% of the neutralized hairstyling polymer, by total weight of the hairstyling formulation and propellant.

7. The aerosol hairspray product according to claim 1, wherein the pressure inside the container is from about 8 bar to about 10 bar, at 50° C.

8. A method for styling hair comprising:
   i. applying to hair an ejected composition, wherein the ejected composition is ejected by the aerosol hairspray product according to claim 1;
   ii. drying the ejected composition on the hair.

* * * * *